US010959413B2

(12) United States Patent
Church et al.

(10) Patent No.: US 10,959,413 B2
(45) Date of Patent: *Mar. 30, 2021

(54) MULTIPLEXED GENOME EDITING

(71) Applicant: President and Fellows of Harvard College, Cambridge, MA (US)

(72) Inventors: George M. Church, Brookline, MA (US); Luhan Yang, Somerville, MA (US); Marc Guell, Barcelona (ES)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/766,551

(22) PCT Filed: Oct. 7, 2016

(86) PCT No.: PCT/US2016/055916
§ 371 (c)(1),
(2) Date: Apr. 6, 2018

(87) PCT Pub. No.: WO2017/062723
PCT Pub. Date: Apr. 13, 2017

(65) Prior Publication Data
US 2018/0288983 A1    Oct. 11, 2018

Related U.S. Application Data

(60) Provisional application No. 62/239,239, filed on Oct. 8, 2015.

(51) Int. Cl.
| C12N 15/63 | (2006.01) |
| C07H 21/02 | (2006.01) |
| C07H 21/04 | (2006.01) |
| A01K 67/027 | (2006.01) |
| C12N 15/113 | (2010.01) |
| C12N 15/85 | (2006.01) |
| C12N 7/00 | (2006.01) |
| C12N 9/22 | (2006.01) |
| C12N 15/11 | (2006.01) |
| C12N 15/90 | (2006.01) |

(52) U.S. Cl.
CPC ...... *A01K 67/0275* (2013.01); *A01K 67/0273* (2013.01); *A01K 67/0276* (2013.01); *C12N 7/00* (2013.01); *C12N 9/22* (2013.01); *C12N 15/11* (2013.01); *C12N 15/1132* (2013.01); *C12N 15/63* (2013.01); *C12N 15/85* (2013.01); *C12N 15/8509* (2013.01); *C12N 15/907* (2013.01); *A01K 2207/05* (2013.01); *A01K 2207/10* (2013.01); *A01K 2227/108* (2013.01); *A01K 2267/025* (2013.01); *C07H 21/02* (2013.01); *C07H 21/04* (2013.01); *C12N 2310/20* (2017.05); *C12N 2740/10062* (2013.01); *C12N 2800/80* (2013.01)

(58) Field of Classification Search
CPC .... C12N 15/63; C12N 2310/20; C07H 21/02; C07H 21/04
USPC ................................ 435/455; 536/23.1, 23.7
See application file for complete search history.

(56) References Cited

U.S. PATENT DOCUMENTS

| 2005/0216964 A1 | 9/2005 | Patience |
| 2005/0266561 A1 | 12/2005 | Wells |
| 2015/0232833 A1 | 8/2015 | Mali et al. |
| 2016/0208243 A1 | 7/2016 | Zhang et al. |
| 2018/0073019 A1 | 3/2018 | Khalili |

FOREIGN PATENT DOCUMENTS

| CN | 105154471 A | 12/2015 |
| EP | 1582591 A2 | 10/2005 |
| WO | 2014/093701 A1 | 6/2014 |
| WO | 2015031775 A1 | 3/2015 |
| WO | 2015/089465 A1 | 6/2015 |
| WO | 2017109177 A1 | 6/2017 |
| WO | 2018144546 A1 | 8/2018 |
| WO | 2018195402 A1 | 10/2018 |

OTHER PUBLICATIONS

Borner et al., Oct. 2014, human Gene therapy, vol. 25, No. 11, pp. A24, Abstract No. OR001.*
Gersbach et al., 2016, US 20160201089 A1, effective filed, Jun. 5, 2013.*
Kaminski et al., Jul. 19, 2015, Journal of the International AIDS Society, vol. 18, Supp. Suppl. 4, pp. 33, Abstract No. TUAA0203.*
Dieckhoff, et al. "Knockdown of porcine endogenous retrovirus (PERV) expression by PE RV-specific sh RNA in transgenic pigs" (Xenotransplantation, vol. 15 No. 1, 2008: pp. 36-45). (Year 2008).
Ericsson, et al (Journal of Virology, Mar. 2001: vol. 75, No. 6, pp. 2765-2770) (Year: 2001).
Fang, et al in "The sequence and analysis of a Chinese pig genome" (GigaScience vol. 1, No. 1, Dec. 1, 2012, pp. 1-11). (Year: 2012).
Karlas, et al (Virology 2004: vol. 325, pp. 18-23). (Year: 2004).
STIC result for Klymiuk et al in J. Gen. Viral. vol. 87, No. 4, pp. 977-986 published Apr. 2006) (Year: 2006).
Semaan, et al in Cytotoxic Effects during Knock Out of Multiple Porcine Endogenous Retrovirus (PERV) Sequences in The Pig Genome by Zinc Finger Nucleases (ZFN) (PLOS ONE published Apr. 24, 2015) (Year: 2015).

(Continued)

*Primary Examiner* — Shin Lin Chen
(74) *Attorney, Agent, or Firm* — Banner & Witcoff, Ltd.

(57) ABSTRACT

A method of modulating some or all copies of a gene in a cell is provided including introducing into a cell one or more ribonucleic acid (RNA) sequences that comprise a portion that is complementary to all or a portion of each of the one or more target nucleic acid sequences, and a nucleic acid sequence that encodes a Cas protein and maintaining the cells under conditions in which the Cas protein is expressed and the Cas protein binds and modulates the one or more target nucleic acid sequences in the cell.

8 Claims, 41 Drawing Sheets

Specification includes a Sequence Listing.

(56) References Cited

OTHER PUBLICATIONS

Semaan, et al in "Long-term effects of PE RV-specific RNA interference in transgenic pigs" (Abstract only of: Xenotransplantation 2012 vol. 19, pp. 112-121). (Year 2012).
Dunn et al., Apr. 1, 2015, FASEB Journal, vol. 29, No. 1_Supplement, Abstract No. LB761.
Third Party Observation filed in PCT/US2016/055916 on Feb. 7, 2018.
Butler et al. "Recent advances in genome editing and creation of genetically modified pigs," International Journal of Surgery, Jul. 29, 2015 (Jul. 29, 2015), vol. 23, Pt. B, pp. 217-222.
Denner, Joachim: "Elimination of porcine endogenous retroviruses from pig cells", Xenotransplantation, Nov. 1, 2015 (Nov. 1, 2015), pp. 411-412, XP055576316, Denmark DOI:10.1111/xen.12210 Retrieved from the internet: URL: file:///C:\Users\FC02424\AppData\Roaming\Mozilla\Firefox\Profiles\FC02424\CiteNPLTemp\CiteNPLWebPage/pdf [retrieved on Apr. 1, 2019].
Niu, Dong et al. "Inactivation of porcine endogenous retrovirus in pigs using CRISPR-Cas9", Science, vol. 357, No. 6357, Aug. 10, 2017 (Aug. 10, 2017), pp. 1303-1307, XP055549027, US ISSN: 0036-8075, DOI: 10.1126/science.aan4187.
Yang, Luhan et al. "Genome-wide inactivation of porcine endogenous retroviruses (PERVs)" Science, Nov. 27PUB Inv, vol. 350, No. 6264, Oct. 11, 2015 (Oct. 11, 2015), pp. 1101-1104, XP055372260, US ISSN: 0036-8075, DOI: 10.1126/science.aad1191.
USPTO, Final Office Action for U.S. Appl. No. 15/888,581. dated Dec. 14, 2018. 19 pages.
USPTO, Notice of Allowance for U.S. Appl. No. 15/888,581. dated Apr. 3, 2019. 7 pages.
EPO, Extended European Search Report for European Patent Application No. 16854392.4. dated Apr. 11, 2019. 13 pages.
Li et al., "Knockdown of Porcine Endogenous Retroviruses by RNA Interference in Chinese Experimental Miniature Pig Fibroblasts," Transplantation Proceedings, vol. 45, No. 2, pp. 748-755 (2013).
Chung et al., "Inhibition of porcine endogenous retrovirus in PK15 cell line by efficient multitargeting RNA interference," Transpl. Int., vol. 27, No. 1, pp. 96-105 (2014).

* cited by examiner

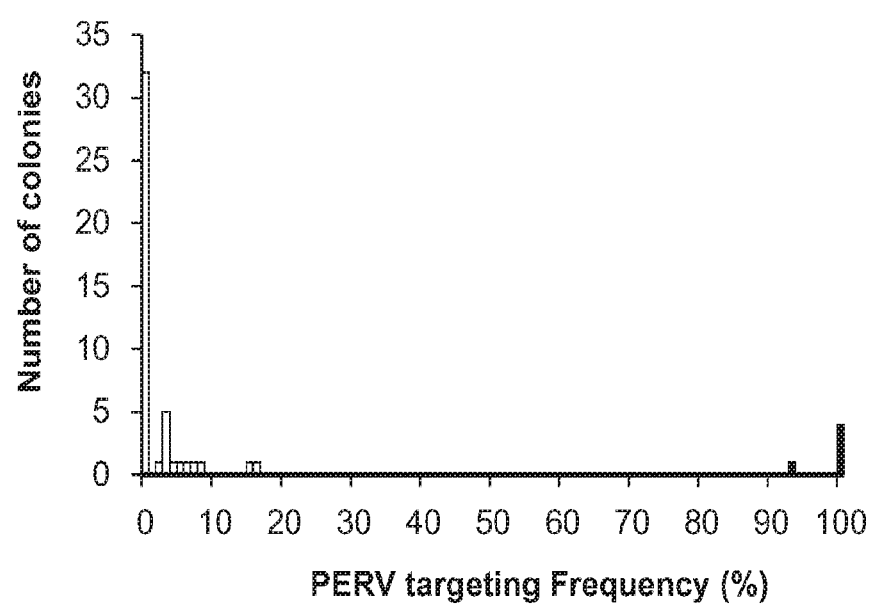

5' GGACCTGGCCAACTTCAGGATCCAAACACCCTCAGGTGACCCTCCT-CCAG-TACGTGGATGACCTGCTTCTGGCGGGAGCCAC 3'
5' GGACC-----A-C----AG-A-----------G---A-------CCAG-TACGTGGATGACCTGCTTCTGGCGGGAGCCAC 3'
5' GGACCTGGCCAACTTCAGGATCCA-------------G-------ACGTGGATGACCTGCTTCTGGCGGGAGCCAC 3'
5' GGACCTGGCCAACTTCAGGATCCAAACACCCTCAGG-------T------G-T-----TGGATGACCTGCTTCTGGCGGGAGCCAC 3'
5' GGACCTGGCCAACTTCAGGATCCAAACACCCTCAGGTGACCCTCCT-CCA-------TGGATGACCTGCTTCTGGCGGGAGCCAC 3'
5' GGACCTGGCCAACTTCAGGATCCAAACACCCTCAGGTGAC---CCT-CCAG-TACGTGGATGACCTGCTTCTGGCGGGAGCCAC 3'
5' GGACCTGGCCAACTTCAGGATCCAAACACCCTCAGGTGACCCTCCT-CCAGTTACGTGGATGACCTGCTTCTGGCGGGAGCCAC 3'
5' GGACCTGGCCAACTTCAGGATCCAAACACCCTCAGGTGACCCTCCTCCCAG-TACGTGGATGACCTGCTTCTGGCGGGAGCCAC 3'

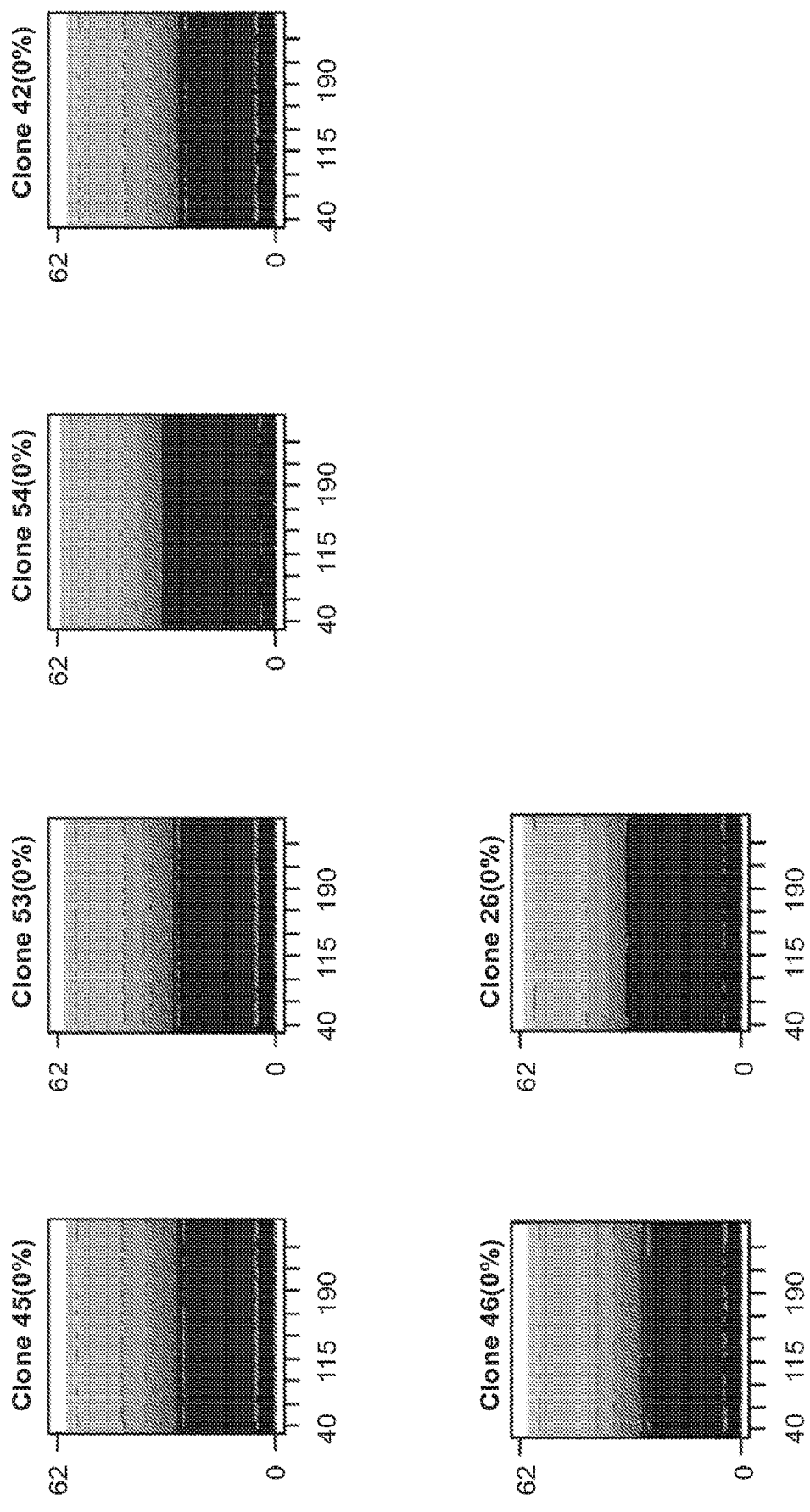

FIG. 16

|  | PK15-1974 | CLONE 15 | CLONE 20 | CLONE 29 | CLONE 38 | CLONE 40 | CLONE 41 |
|---|---|---|---|---|---|---|---|
| Chromosome 1 | | | | | | | |
| Chromosome 2 | | add(2)(p14.2) | | add(2)(p14.2) | add(2)(p14.2) | | add(2)(p14.2) |
| Chromosome 3 | add(3)p15 | add(3)(p15) | add(3)(p15) | add(3)(p15) | add(3)(p15) | add(3)p15 | add(3)(p15) |
| Chromosome 4 | | (+4) | (+4,+4) | add(4)(p13.1) | add(4)(p15.1), add(4)(p13.1) | (+4,+4,+4) | (+4) |
| Chromosome 5 | -5 | -5 | -5 | -5 | -5 | (-5,-5) | -5 |
| Chromosome 6 | -6 | | | | | | |
| Chromosome 7 | -7 | -7 | der(7;16)(q10;q10) | -7 | -7 | der(7;16)(q10;q10) | -7 |
| Chromosome 8 | | | | | | | |
| Chromosome 9 | -9 | | | | | | |
| Chromosome 10 | -10 | -10 | -10 | -10 | -10 | -10 | -10 |
| Chromosome 11 | -11 | | | | | | |
| Chromosome 12 | | | | | | | |
| Chromosome 13 | | | | | | | |
| Chromosome 14 | t | der(14;15)(q10;q10), add(14)(p10) | der(14;15)(q10;q10), add(14)(p10) | der(14;15)(q10;q10), add(14)(p10) | der(14;15)(q10;q10), add(14)(p10) | der(14;15)(q10;q10), add(14)(p10) | der(14;15)(q10;q10), add(14)(p10) |
| Chromosome 15 | | | | | | | |
| Chromosome 16 | | -16 | | -16 | -16 | -16 | -16 |
| Chromosome 17 | (-17)i(17)(q10) | (-17)i(17)(q10) | (-17)i(17)(q10) | (-17)i(17)(q10) | (-17)i(17)(q10) | (-17)i(17)(q10) | (-17)i(17)(q10) |
| Chromosome 18 | | | | | | | |
| X,Y | XX | XX | XX | XX | XX | XX | XX |
| A | n/a | +4mar [8] | +1~5mar [cp10] | +4mar [9] | +3~4mar [cp10] | +1~5mar [cp10] | +4mar [5] |

FIG. 17

| Nomenclature | Meaning |
|---|---|
| + | gain of a chromosome |
| - | loss of a chromosome |
| (:) | break (in detailed descriptions) |
| () | Surround structurally altered chromosomes and breakpoints |
| add | additional material of unknown origin |
| der | derivative chromosome |
| i | isochromosome |
| p | short arm of a chromosome |
| q | long arm of a chromosome |
| t | translocation |
| a | abnormality |

FIG. 18
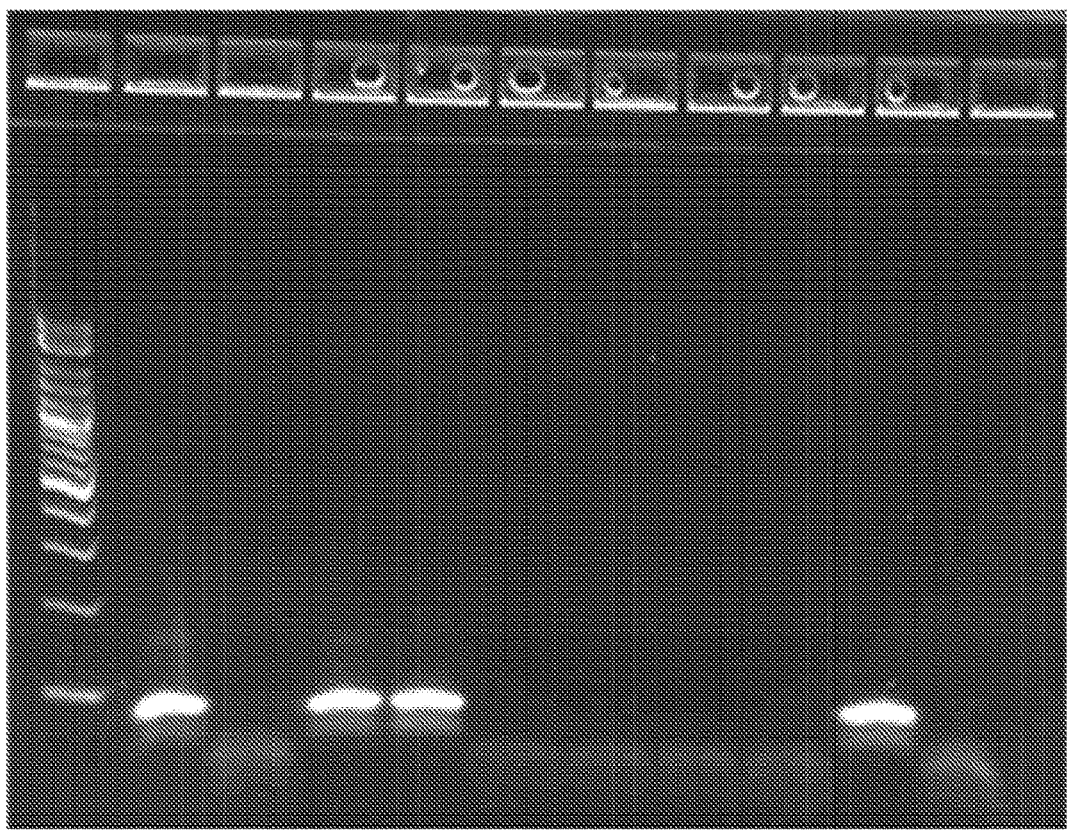
FIG. 19
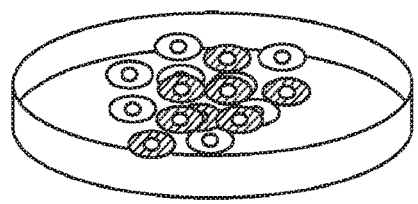
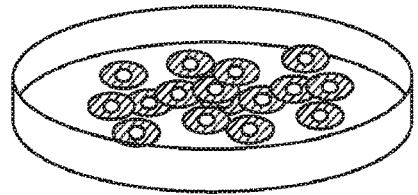

FIG. 23A
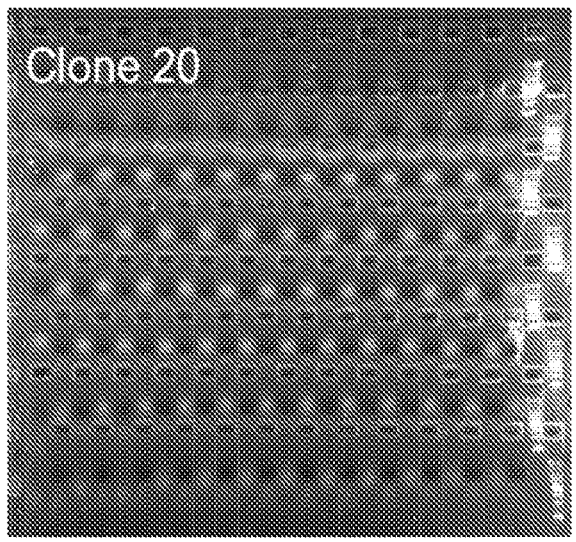
FIG. 23B
FIG. 23C
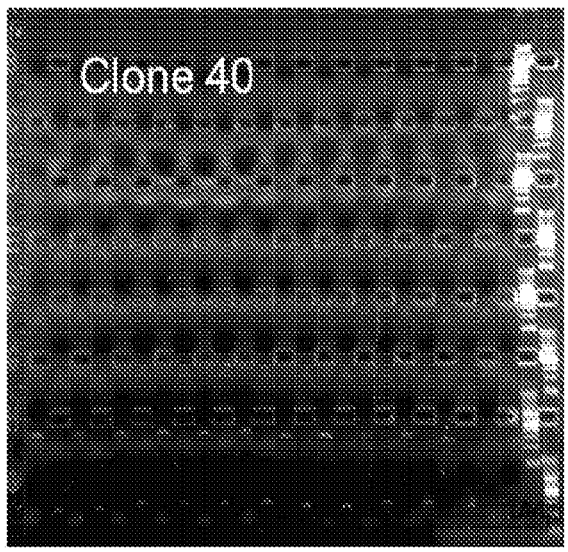
FIG. 23D
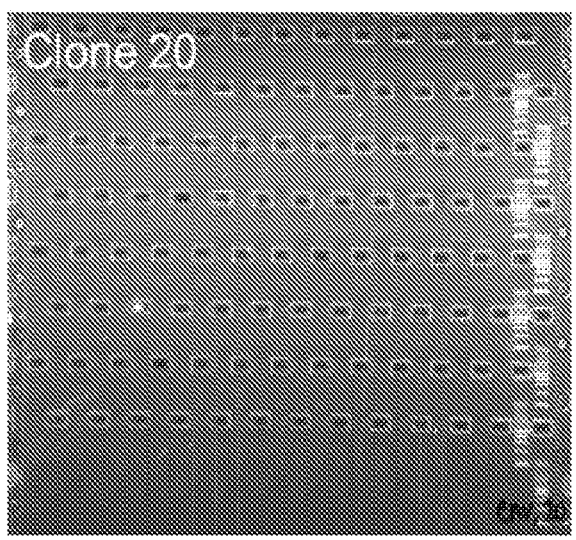
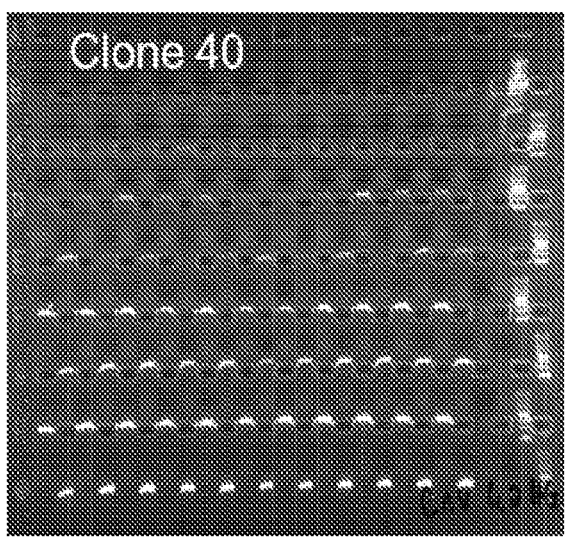

| | Clone 15 | Clone 20 | Clone 29 | Clone 38 | Clone 40 | Clone 41 | PK15 |
|---|---|---|---|---|---|---|---|
| Cas9 | 782 | 771 | 207 | 416 | 61 | 78 | 0 |
| gRNA1 | 5 | 3 | 2 | 1 | 0 | 0 | 0 |
| gRNA2 | 4 | 4 | 2 | 1 | 0 | 0 | 0 |
| Total | 75815790 | 72609563 | 82295929 | 72569325 | 60990510 | 80508090 | 0 |

FIG. 27B

| Sample | Name |
|---|---|
| | KRT18 |
| | IL1A |
| | CCND2 |
| | CD14 |
| | NEFH |
| | CD44 |
| | CD38 |
| | EREG |
| | ENO2 |
| | BTG2 |
| | SAT1 |
| | SATB1 |
| | FAS |
| | GPX3 |
| | PLCB2 |
| | ERBB2 |
| | PMAIP1 |
| | IER3 |
| | TNFSF10 |
| | IGFBP6 |
| | XIAP |
| | CASP3 |
| | IFNGR1 |
| | ATF3 |
| | BCL2L2 |
| | BNIP3I |
| | TIMP1 |
| | CIM |
| | RETSAT |
| | PSEN1 |
| | DNAJC3 |
| | PFA15 |
| | IL18 |
| | APP |
| | LEE1 |
| | RHDB |
| | CLU |
| | PNASEL |
| | MCL1 |
| | PDCD4 |
| | BMP2 |
| | TNFRSF12A |
| | SDD2 |
| | CINNB1 |
| | BAX |
| | ERBB3 |
| | ANXA1 |
| | LGALS3 |
| | SDSIM1 |
| | ETF1 |
| | EBP |
| | LMNA |
| | GPX4 |
| | TIMP3 |
| | BCAP31 |

| | |
|---|---|
| | PLAT |
| | CYLD |
| | CAV1 |
| | CASP9 |
| | F2R |
| | NFDD9 |
| | AIFM3 |
| | CCND1 |
| | SPTAN1 |
| | BARA |
| | WEE1 |
| | CBFRRP |
| | PDGFRB |
| | GSR |
| | TSPO |
| | ADD1 |
| | IMGB2 |
| | ANKH |
| | RDCK1 |
| | PPP2RSB |
| | TGFBR3 |
| | ISG20 |
| | BTG3 |
| | GADD45B |
| | RFLA |
| | DPYD |
| | CDC25B |
| | IRF1 |
| | MADD |
| | DFFA |
| | SDD1 |
| | CASP2 |
| | BID |
| | TDP2A |
| | RHDT2 |
| | IGF2R |
| | BCL10 |
| | PSEN2 |
| | TXNIP |
| | CD2 |
| | PAK1 |
| | DNAJA1 |
| | BRCA1 |
| | CDK2 |
| | HSPB1 |
| | TGFB2 |
| | FDXR |
| | TAP1 |
| | PTK2 |
| | CASP6 |
| | MGMT |
| | SMAD7 |
| | MMP2 |
| | F2 |

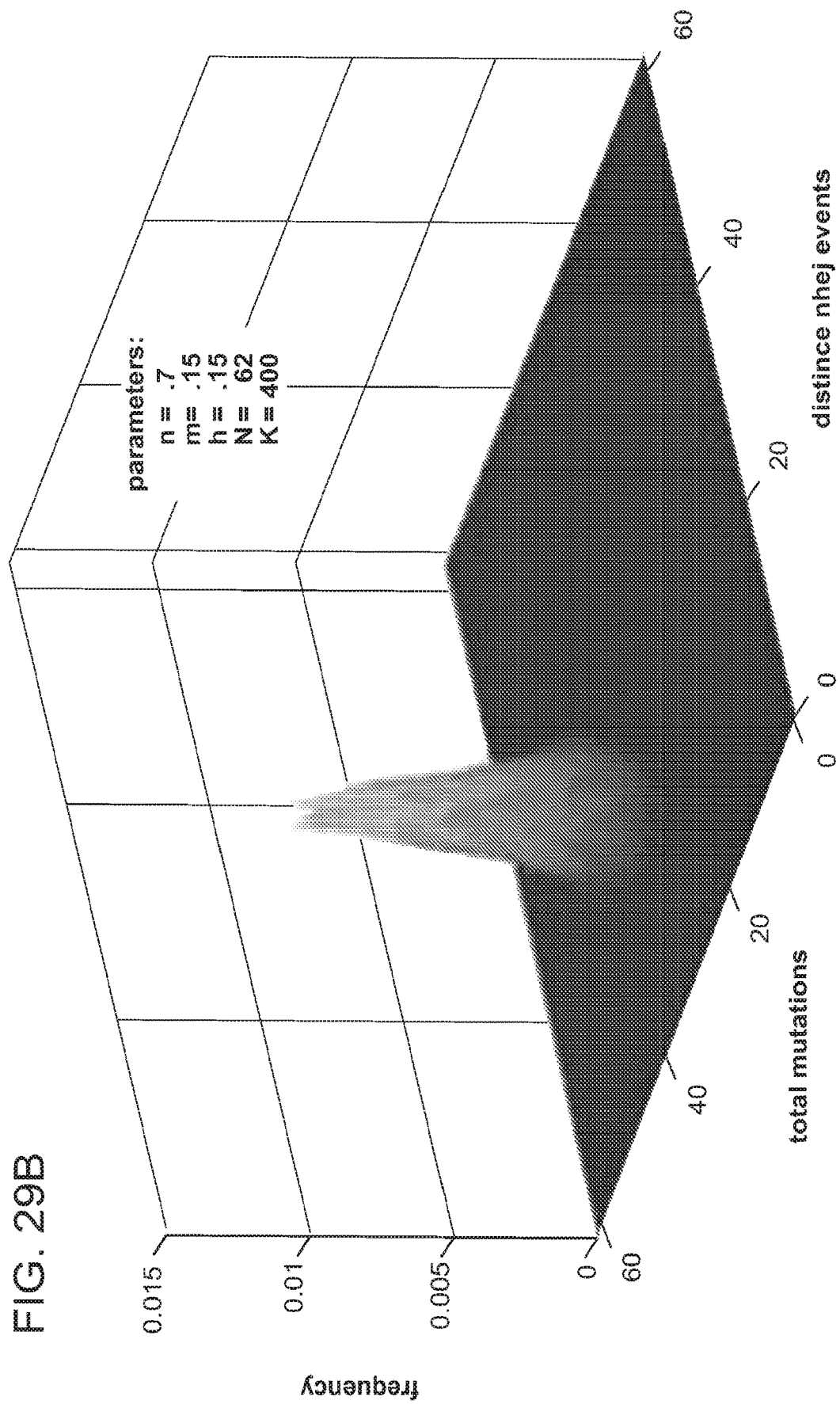

US 10,959,413 B2

MULTIPLEXED GENOME EDITING

RELATED APPLICATIONS

This application is a National Stage Application under 35 U.S.C. 371 of co-pending PCT application PCT/US2016/055916 designating the United States and filed Oct. 7, 2016; which claims the benefit of U.S. provisional application No. 62/239,239 and filed Oct. 8, 2015 each of which are hereby incorporated by reference in their entireties.

STATEMENT OF GOVERNMENT INTERESTS

This invention was made with government support under HG005550 awarded by the National Institutes of Health. The government has certain rights in the invention.

BACKGROUND OF THE INVENTION

Genome editing via sequence-specific nucleases is known. A nuclease-mediated double-stranded DNA (dsDNA) break in the genome can be repaired by two main mechanisms: Non-Homologous End Joining (NHEJ), which frequently results in the introduction of non-specific insertions and deletions (indels), or homology directed repair (HDR), which incorporates a homologous strand as a repair template. See reference 4 hereby incorporated by reference in its entirety. When a sequence-specific nuclease is delivered along with a homologous donor DNA construct containing the desired mutations, gene targeting efficiencies are increased by 1000-fold compared to just the donor construct alone.

Alternative methods have been developed to accelerate the process of genome modification by directly injecting DNA or mRNA of site-specific nucleases into the one cell embryo to generate DNA double strand break (DSB) at a specified locus in various species. DSBs induced by these site-specific nucleases can then be repaired by either error-prone non-homologous end joining (NHEJ) resulting in mutant mice and rats carrying deletions or insertions at the cut site. If a donor plasmid with homology to the ends flanking the DSB is co-injected, high-fidelity homologous recombination can produce animals with targeted integrations. Because these methods require the complex designs of zinc finger nucleases (ZNFs) or Transcription activator-like effector nucleases (TALENs) for each target gene and because the efficiency of targeting may vary substantially, no multiplexed gene targeting has been reported to date.

Thus, improved methods for producing genetically modified cells to generate animals, such as pigs, are needed for potential sources of organs for transplantation.

SUMMARY OF THE INVENTION

Described herein is the use of the Clustered Regularly Interspaced Short Palindromic Repeats (CRISPR) and CRISPR associated (Cas) proteins (CRISPR/Cas) system to achieve highly efficient and simultaneous targeting of multiple nucleic acid sequences in cells.

Aspects of the present disclosure are directed to the modification of genomic DNA, such as multiplex modification of DNA, in a cell (e.g., stem cell, somatic cell, germ line cell, zygote) using one or more guide RNAs (ribonucleic acids) to direct an enzyme having nuclease activity expressed by the cell, such as a DNA binding protein having nuclease activity, to a target location on the DNA (deoxyribonucleic acid) wherein the enzyme cuts the DNA and an exogenous donor nucleic acid is inserted into the DNA, such as by homologous recombination. Aspects of the present disclosure include cycling or repeating steps of DNA modification in a cell to create a cell having multiple modifications of DNA within the cell. Modifications can include insertion of exogenous donor nucleic acids. Modifications can include deletion of endogenous nucleic acids.

Multiple nucleic acid sequences can be modulated (e.g., inactivated) by a single step of introducing into a cell, which expresses an enzyme, and nucleic acids encoding a plurality of RNAs, such as by co-transformation, wherein the RNAs are expressed and wherein each RNA in the plurality guides the enzyme to a particular site of the DNA, the enzyme cuts the DNA. According to this aspect, many alterations or modification of the DNA in the cell are created in a single cycle.

According to one aspect, the cell expressing the enzyme has been genetically altered to express the enzyme such as by introducing into the cell a nucleic acid encoding the enzyme and which can be expressed by the cell. In this manner, aspects of the present disclosure include cycling the steps of introducing RNA into a cell which expresses the enzyme, introducing exogenous donor nucleic acid into the cell, expressing the RNA, forming a co-localization complex of the RNA, the enzyme and the DNA, and enzymatic cutting of the DNA by the enzyme. Insertion of a donor nucleic acid into the DNA is also provided herein. Cycling or repeating of the above steps results in multiplexed genetic modification of a cell at multiple loci, i.e., a cell having multiple genetic modifications.

According to certain aspects, DNA binding proteins or enzymes within the scope of the present disclosure include a protein that forms a complex with the guide RNA and with the guide RNA guiding the complex to a double stranded DNA sequence wherein the complex binds to the DNA sequence. According to one aspect, the enzyme can be an RNA guided DNA binding protein, such as an RNA guided DNA binding protein of a Type II CRISPR System that binds to the DNA and is guided by RNA. According to one aspect, the RNA guided DNA binding protein is a Cas9 protein.

This aspect of the present disclosure may be referred to as co-localization of the RNA and DNA binding protein to or with the double stranded DNA. In this manner, a DNA binding protein-guide RNA complex may be used to cut multiple sites of the double stranded DNA so as to create a cell with multiple genetic modifications, such as disruption of one or more (e.g., all) copies of a gene.

According to certain aspects, a method of making multiple alterations to target DNA in a cell expressing an enzyme that forms a co-localization complex with RNA complementary to the target DNA and that cleaves the target DNA in a site specific manner is provided including (a) introducing into the cell a first foreign nucleic acid encoding one or more RNAs complementary to the target DNA and which guide the enzyme to the target DNA, wherein the one or more RNAs and the enzyme are members of a co-localization complex for the target DNA, wherein the one or more RNAs and the enzyme co-localize to the target DNA, the enzyme cleaves the target DNA to produce altered DNA in the cell, and repeating step (a) multiple times to produce multiple alterations to the DNA in the cell.

In some aspects, a method of inactivating expression of one or more target nucleic acid sequences in a cell comprises introducing into a cell one or more ribonucleic acid (RNA) sequences that comprise a portion that is complementary to all or a portion of each of the one or more target nucleic acid sequences, and a nucleic acid sequence that encodes a Cas protein; and maintaining the cells under conditions in which the Cas protein is expressed and the Cas protein binds and inactivates the one or more target nucleic acid sequences in the cell.

In other aspects, a method of modulating one or more target nucleic acid sequences in a cell comprises introducing into the cell a nucleic acid sequence encoding an RNA complementary to all or a portion of a target nucleic acid sequence in the cell; introducing into the cell a nucleic acid sequence encoding an enzyme that interacts with the RNA and cleaves the target nucleic acid sequence in a site specific manner; and maintaining the cell under conditions in which the RNA binds to complementary target nucleic acid sequence forming a complex, and wherein the enzyme binds to a binding site on the complex and modulates the one or more target nucleic acid sequences.

In the methods described herein, the introducing step can comprise transfecting the cell with the one or more RNA sequences and the nucleic acid sequence that encodes the Cas protein.

In some embodiments, the one or more RNA sequences, the nucleic acid sequence that encodes the Cas protein, or a combination thereof are introduced into a genome of the cell.

In some embodiments, the expression of the Cas protein is induced.

In the methods described, herein the cell is from an embryo. The cell can be a stem cell, zygote, or a germ line cell. In embodiments where the cell is a stem cell, the stem cell is an embryonic stem cell or pluripotent stem cell. In other embodiments, the cell is a somatic cell. In embodiments, where the cell is a somatic cell, the somatic cell is a eukaryotic cell or prokaryotic cell. The eukaryotic cell can be an animal cell, such as from a pig, mouse, rat, rabbit, dog, horse, cow, non-human primate, human.

The one or more target nucleic acid sequences can comprise a porcine endogenous retrovirus (PERV) gene. For example, the PERV gene can comprise a pol gene.

The methods described herein can inactivate, modulate, or effect one or more copies of the pol gene. In some embodiments, all copies of the pol gene in the cell are inactivated.

In some embodiments, the Cas protein is a Cas9.

In some embodiments, the one or more RNA sequences can be about 10 to about 1000 nucleotides. For example, the one or more RNA sequences can be about 15 to about 200 nucleotides.

In some aspects an engineered cell comprises one or more endogenous viral genes; and one or more exogenous nucleic acid sequences that comprise a portion that is complementary to all or a portion of one or more target nucleic acid sequences of the one or more endogenous viral genes; wherein each of the one or more endogenous viral genes of the cell are modulated.

In another aspect, an engineered cell can comprise a plurality of endogenous retroviral genes; and one or more exogenous nucleic acid sequences that comprise a portion that is complementary to all or a portion of one or more target nucleic acid sequences of the plurality of endogenous viral genes; wherein each of the plurality of endogenous viral genes of the cell are modulated.

The engineered cells described herein can comprise a porcine endogenous retrovirus (PERV) gene. For example, the PERV gene can comprise a pol gene.

In some aspects, modulation of the pol gene inactivates one or more copies of the pol gene. For example, all or substantially all copies of the pol gene in the cell are inactivated.

According to one aspect, the RNA is between about 10 to about 1000 nucleotides. According to one aspect, the RNA is between about 20 to about 100 nucleotides.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

BRIEF DESCRIPTION OF THE DRAWINGS

FIGS. 2A-2B illustrate clonal PK15 cells with inactivation of all copies of PREV pol genes after Cas9 treatment. (A) A bimodal distribution of pol targeting efficiencies was observed among the single-cell-derived PK15 clones after 17 days of Cas9 induction. 45/50 exhibited <16% targeting efficiency; 5/50 clones exhibited >93% targeting efficiency. (B) PK15 haplotypes at PERV pol loci after CRISPR-Cas9 treatment. In red, indel events in the PERV pol sequence are represented. Shades of purple indicate endogenous PERVs.

FIG. 10 (S7) illustrates Sanger sequencing validation of PERV targeting efficiency and indel patterning. (SEQ ID NO:29 represents the complete sequence of the 8 sequence fragments as shown.)

FIG. 16 (S13) illustrates Summary of karyotype analysis of PK15 clones.

FIG. 17 (S14) illustrates Karyotype nomenclature.

FIG. 18 (S15) illustrates Detection of PERV reverse transcriptase activity.

FIG. 19 (S16) illustrates an experimental design to detect the transmission of PERVs to human cells.

FIGS. 23A-23D (S20) illustrates detection of PERV DNA elements in HEK293 cells using PERV env primers.

FIGS. 27A-27B (S24) illustrate gene set enrichment analysis.

FIGS. 29A-29D (S26) illustrates a Markov model analysis of DNA repair processes leading to Cas9 elimination of active PERV elements.

DETAILED DESCRIPTION OF THE INVENTION

Aspects of the present invention are directed to the use of CRISPR/Cas9, for nucleic acid engineering. Described herein is the development of an efficient technology for the generation of animals (e.g., pigs) carrying multiple mutated genes. Specifically, the clustered regularly interspaced short palindromic repeats (CRISPR) and CRISPR associated genes (Cas genes), referred to herein as the CRISPR/Cas system, has been adapted as an efficient gene targeting technology e.g., for multiplexed genome editing. Demonstrated herein is that CRISPR/Cas mediated gene editing allows the simultaneous inactivation of 62 copies of the porcine endogenous retrovirus (PERV) pol gene in a porcine kidney epithelial cell line (e.g., PK15) with high efficiency. Co-injection or transfection of Cas9 mRNA and guide RNA (gRNA) targeting PERVs into cells generated a greater than 1000 fold reduction in PERV transmission to human cells with biallelic mutations in both genes with an efficiency of up to 100%. Shown herein is that the CRISPR/Cas system allows the one step generation of cells carrying inactivation of all copies of PERV. In certain embodiments a method described herein generates cell and animals, e.g., pigs, with inactivation of 1, 2, 3, 4, 5, or more genes with an efficiency of between 20% and 100%, e.g., at least 20%, 30%, 40%, 50%, 60%, 70%, 80%, 85%, 90%, 95%, or more, e.g., up to 96%, 97%, 98%, 99%, or more.

EXEMPLIFICATION

Example 1. Genome-Wide Inactivation of Porcine Endogenous Retroviruses (PERVs)

The shortage of organs for transplantation is a major barrier to the treatment of organ failure. While porcine organs are considered promising, their use has been checked by concerns about transmission of porcine endogenous retroviruses (PERVs) to humans. Here, the eradication of all PERVs in a porcine kidney epithelial cell line (PK15) was performed. It was first determined the PK15 PERV copy number to be 62. Using CRISPR-Cas9, all 62 copies of the PERV pol gene were disrupted and demonstrated a >1000-fold reduction in PERV transmission to human cells using our engineered cells. This study showed that CRISPR-Cas9 multiplexability can be as high as 62 and demonstrates the possibility that PERVs can be inactivated for clinical application to porcine-to-human xenotransplantation.

Pig genomes contain from a few to several dozen copies of PERV elements. Unlike other zoonotic pathogens, PERVs cannot be eliminated by biosecure breeding. Prior strategies for reducing the risk of PERV transmission to humans have included small interfering RNAs (RNAi), vaccines, and PERV elimination using zinc finger nucleases and TAL effector nucleases, but these have had limited success. Here, the successful use of the CRISPR-Cas9 RNA-guided nuclease system can be used to inactivate all copies of the PERV pol gene and effect a 1000-fold reduction of PERV infectivity of human cells.

Figure 1A:
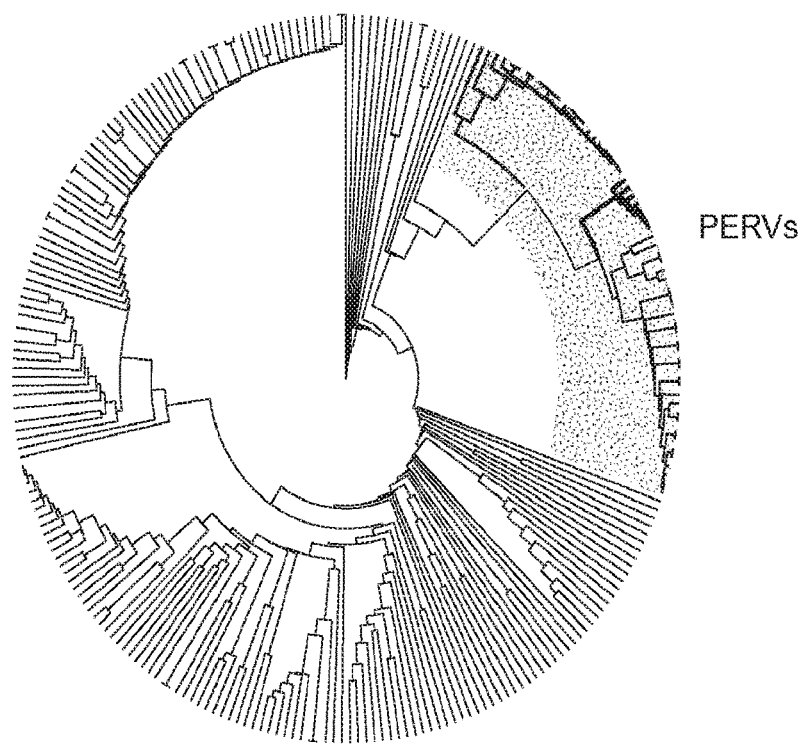
FIGS. 1A-1C illustrate CRISPR-Cas9 gRNAs were designed to specifically target the pol gene in 62 copies of PERVs in PK15 cells. (A) Phylogenetic tree representing endogenous retroviruses present in the pig genome. PERVs are highlighted in blue. (B) Copy number determination of PERVs in PK15 cells via digital droplet PCR. The copy number of pol elements was estimated to be 62 using three independent reference genes: ACTB, GAPDH, and EB2. N=3, mean+/−SEM. (C) Two CRISPR-Cas9 gRNAs were designed to target the catalytic region of the PERV pol gene. The two gRNA targeting sequences are shown below a schematic of PERV gene structure. Their PAM sequences are highlighted in red. (SEQ ID NO:27-28)
Figure 1B:
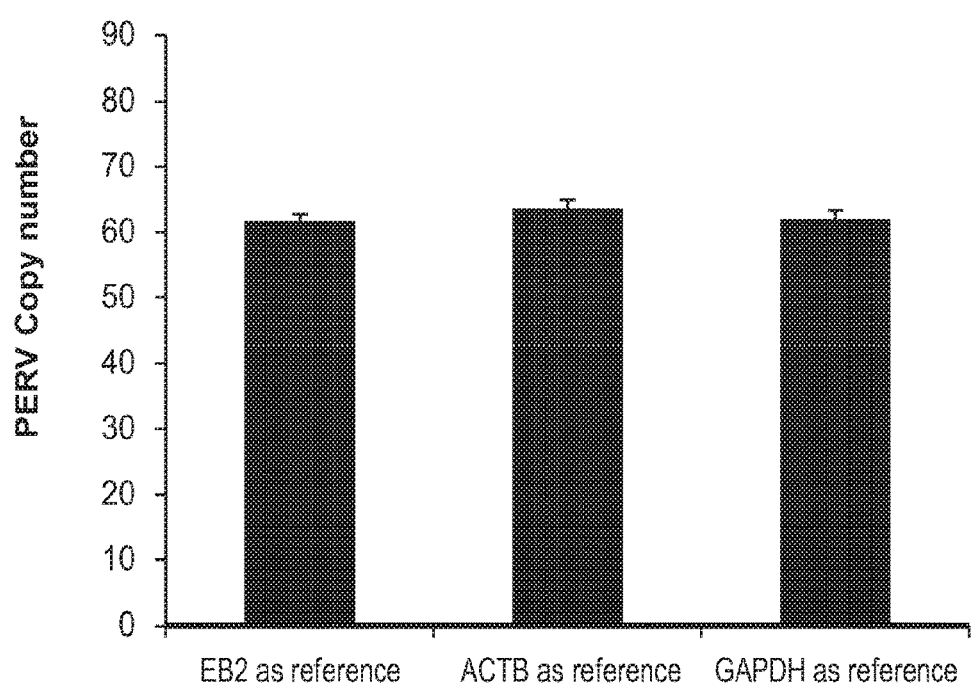
Figure 1C:
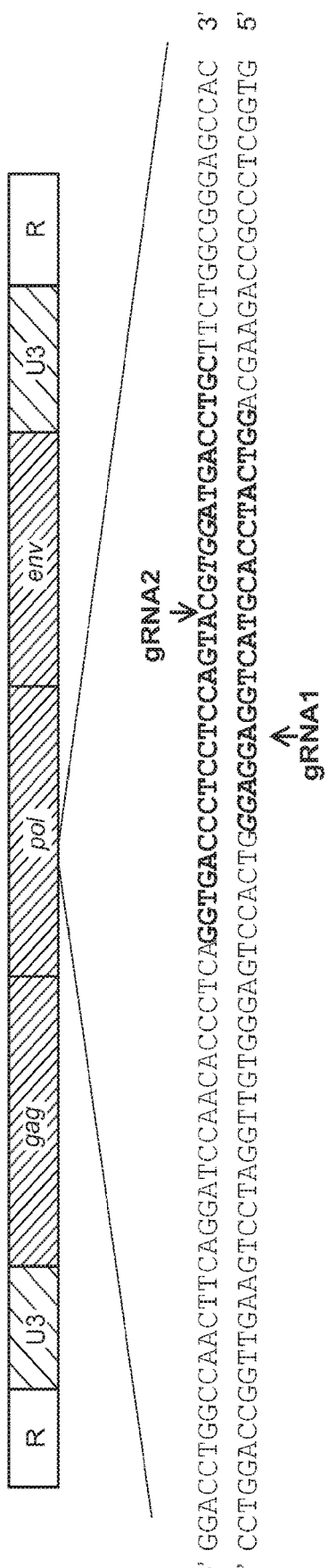
Figure 4:
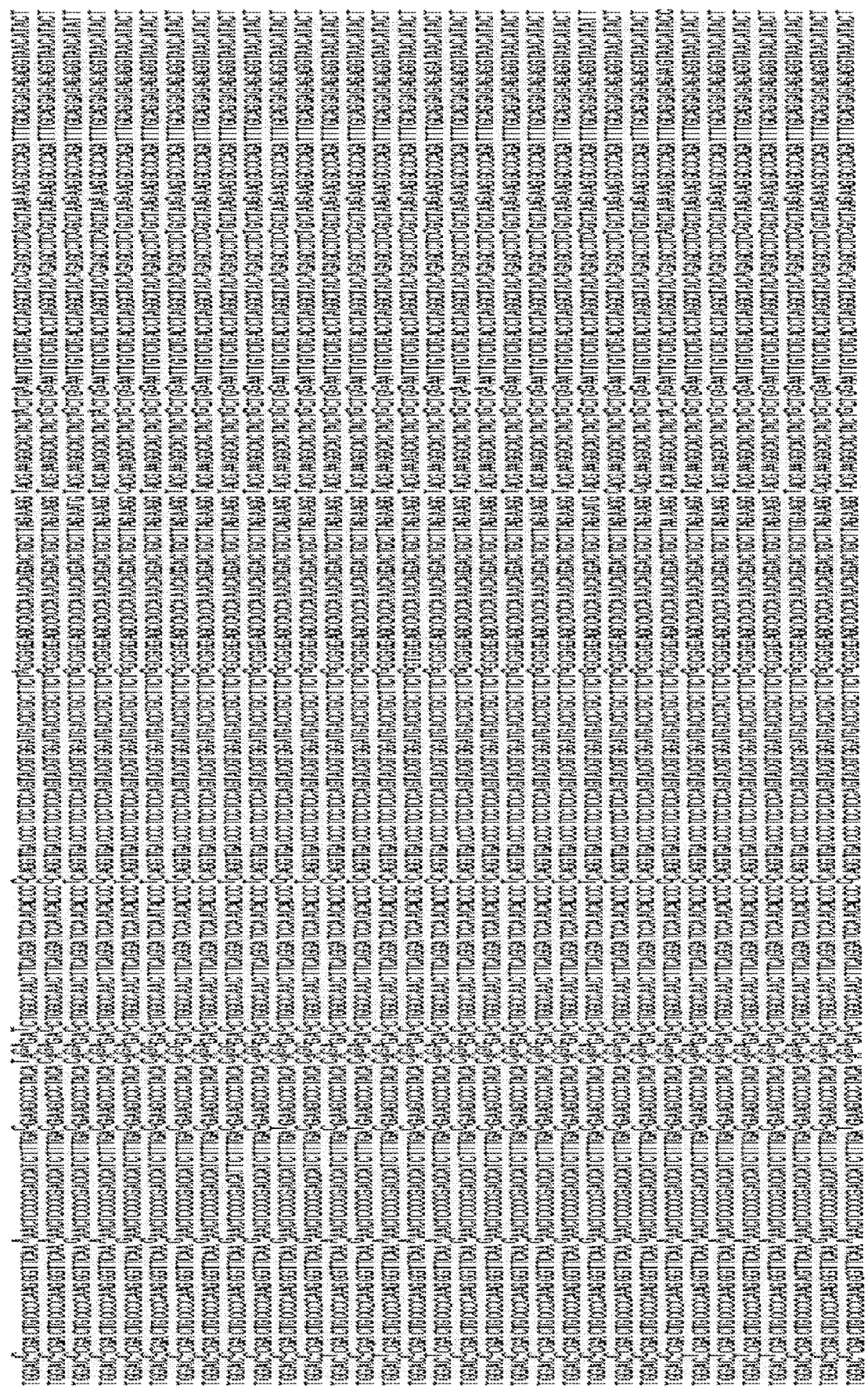
FIG. 4 (S1) illustrates PERV pol consensus sequence and gRNA design (SEQ ID NOS:281-342).

To design Cas9 guide RNAs (gRNAs) that specifically target PERVs, the sequences of publically available PERVs and other endogenous retroviruses in pigs (Methods) were analyzed. A distinct clade of PERV elements (FIG. 1A) were identified and determined there to be 62 copies of PERVs in PK15 cells using droplet digital PCR (FIG. 1B). Two Cas9 guide RNAs (gRNAs) were designed that targeted the highly conserved catalytic center of the pol gene on PERVs (FIG. 1C, FIG. 4). The pol gene product functions as a reverse transcriptase (RT) and is thus essential for viral replication and infection. It was determined that these gRNAs targeted all PERVs but no other endogenous retrovirus or other sequences in the pig genome (Methods).

Figure 5:
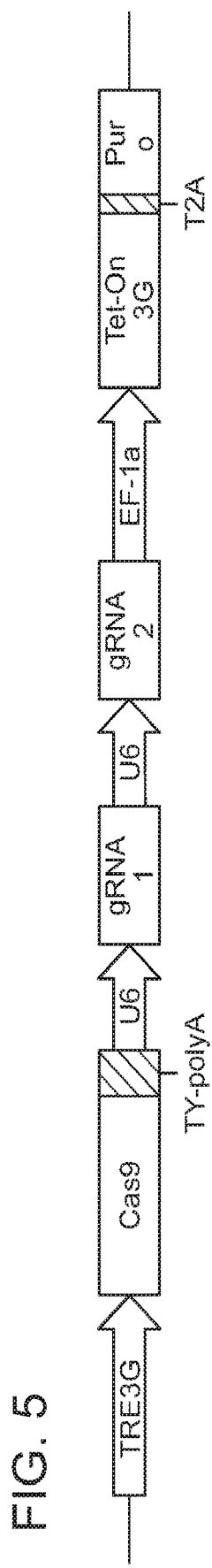
FIG. 5 (S2) is a schematic of CRISPR/Cas9 construct targeting PERVs.
Figure 6:
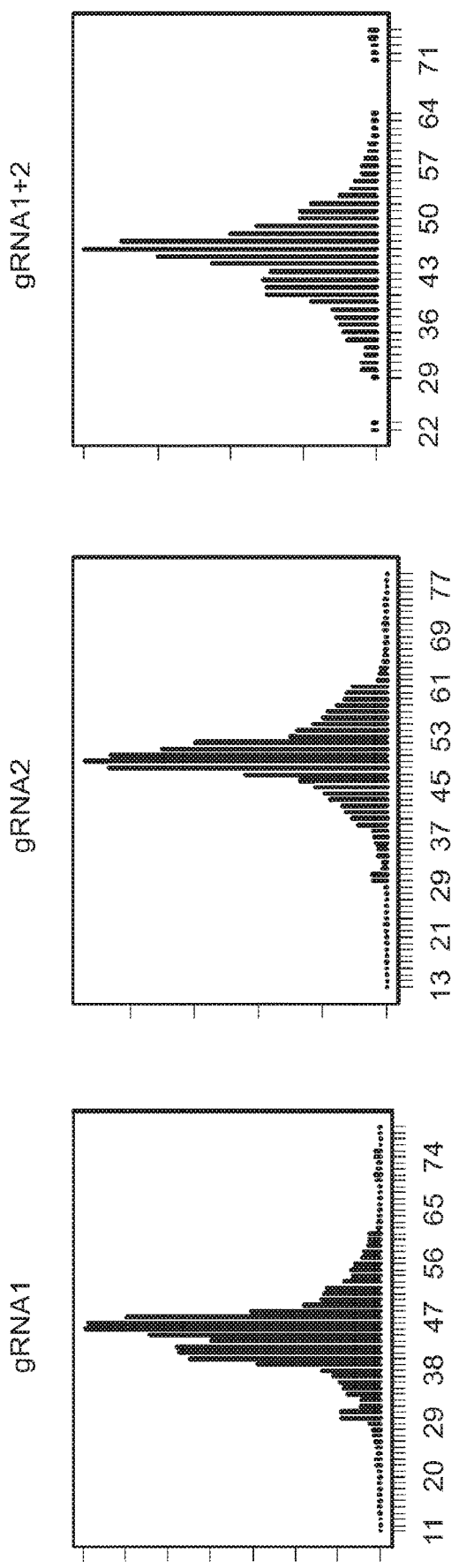
FIG. 6 (S3) illustrates measurement of Cas9-gRNAs activity.
Figure 7:
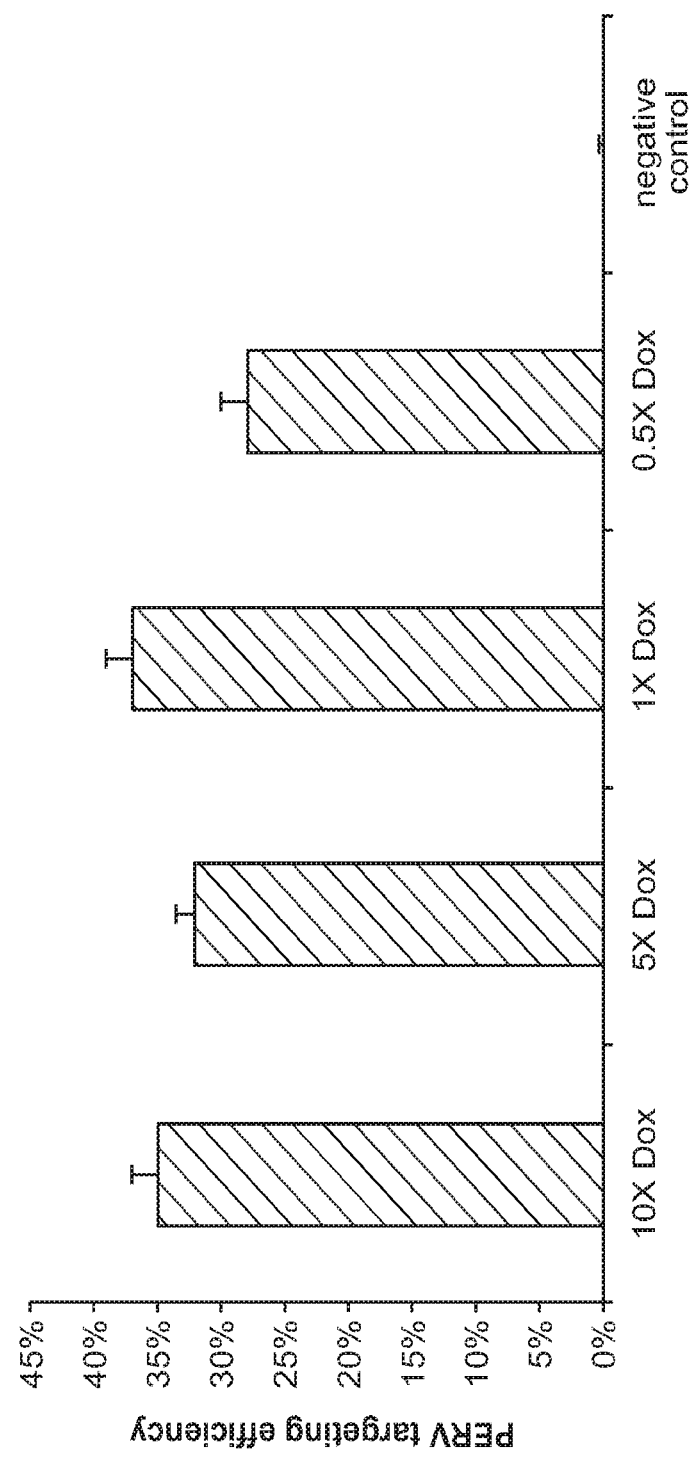
FIG. 7 (S4) illustrates optimization of DOX concentration to induce Cas9 expression for PERV targeting.
Figure 8:
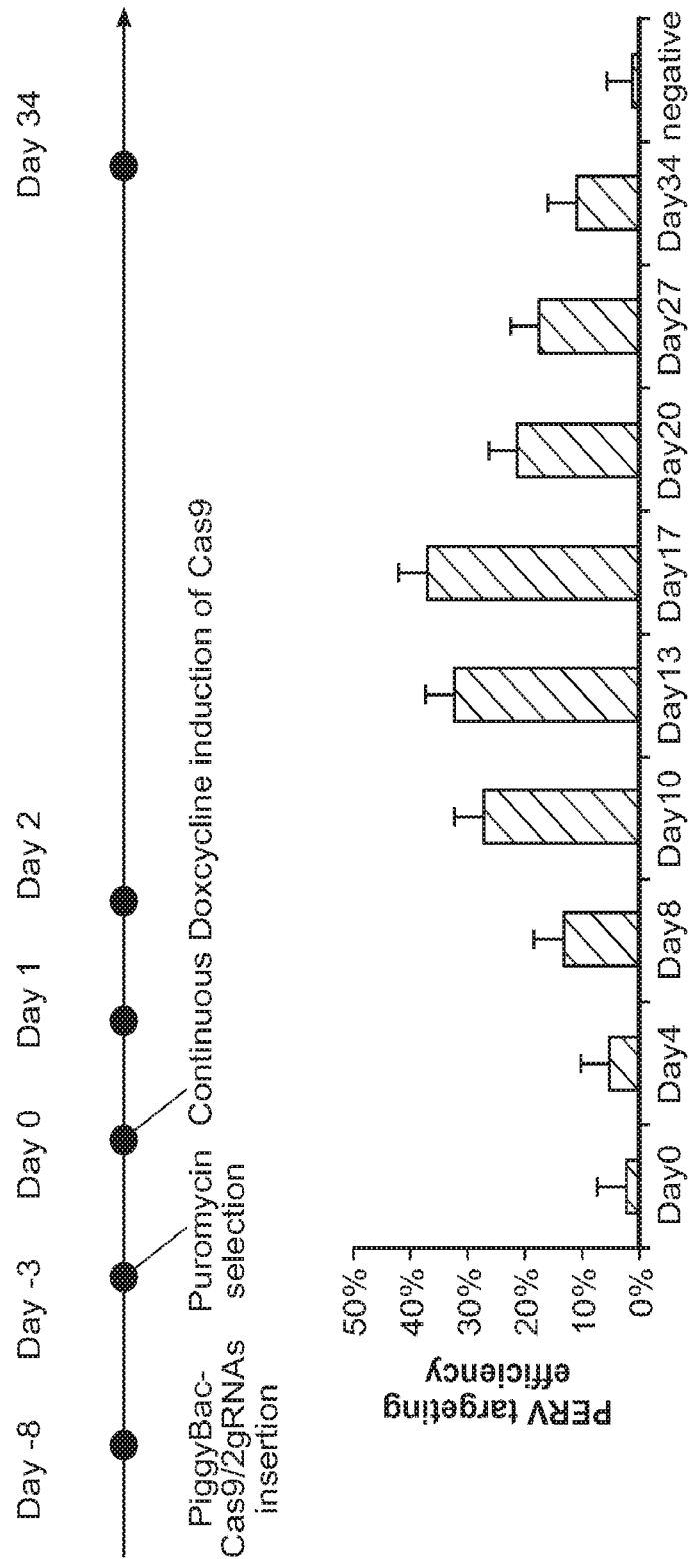
FIG. 8 (S5) illustrates time series measurement of Piggybac-Cas9/gRNAs PERV targeting efficiencies.
Figure 9:
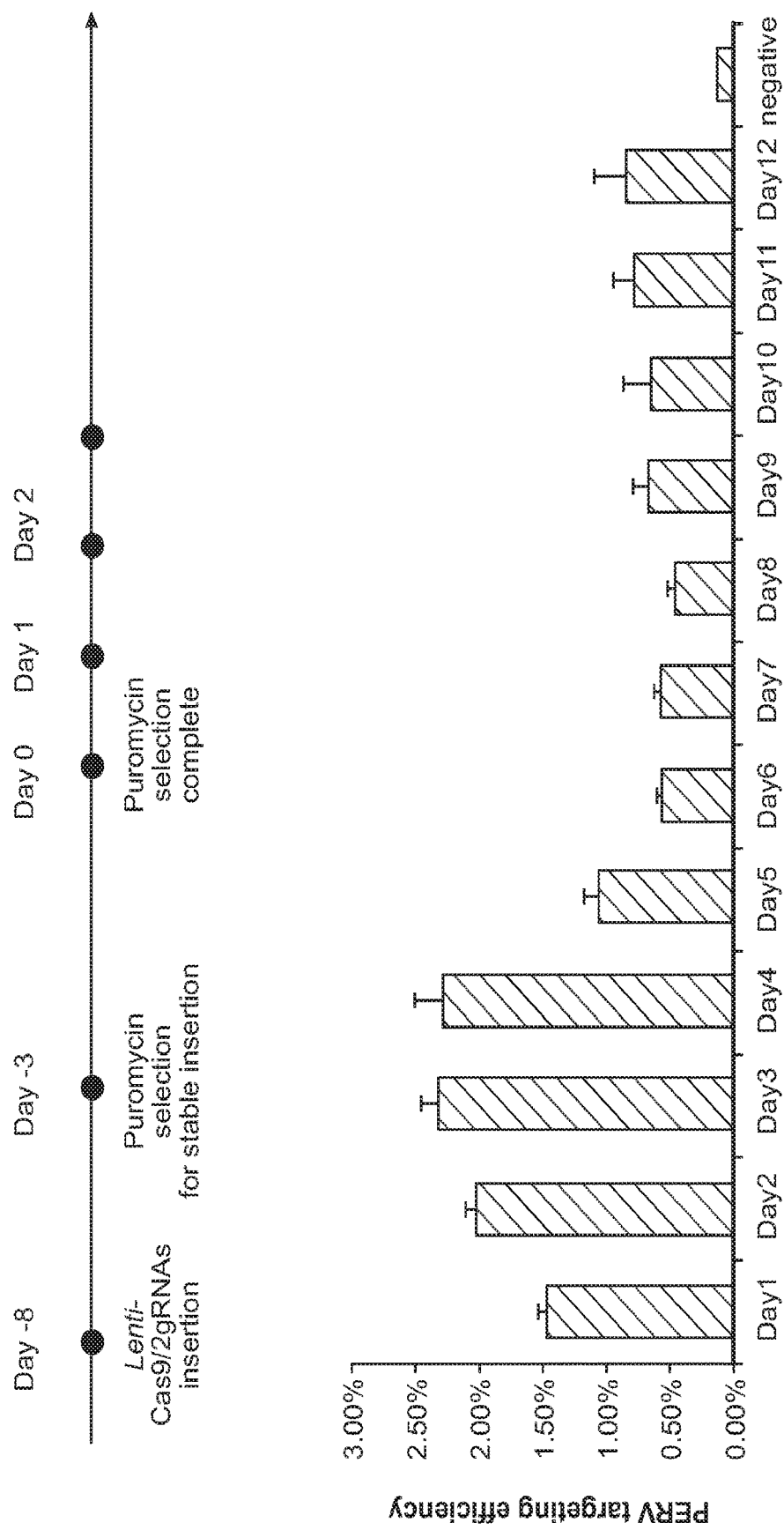
FIG. 9 (S6) illustrates time series measurement of Lenti-Cas9/2gRNAs PERV targeting efficiency.
Figure 11:
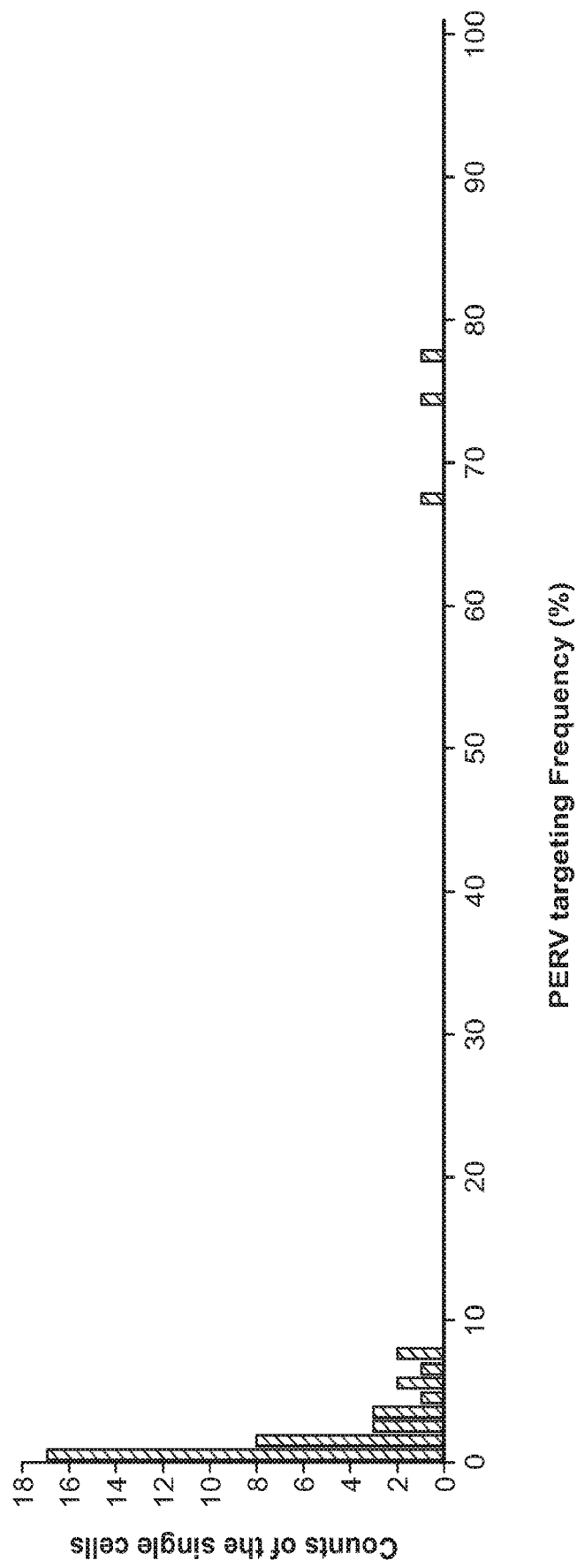
FIG. 11 (S8) illustrates repeated the gene editing experiment.
Figure 12A:
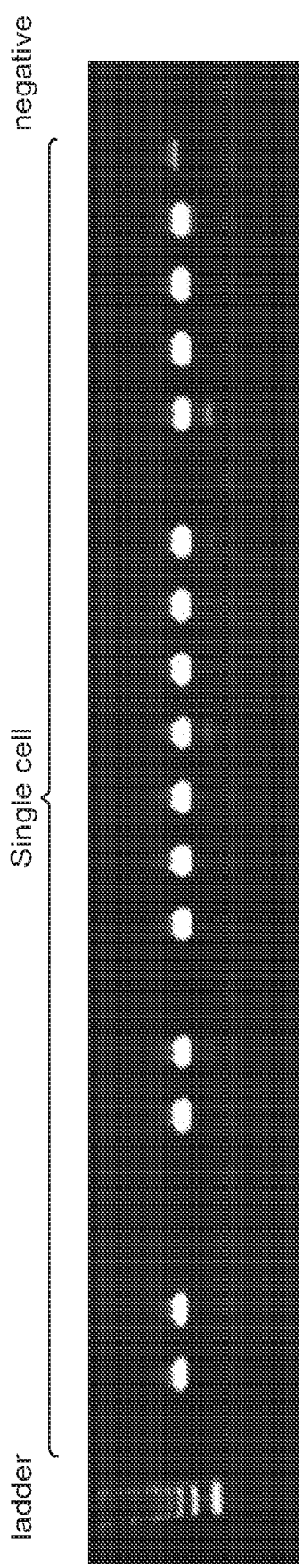
FIGS. 12A-B (S9) illustrates PERV pol targeting efficiency of single cells.
Figure 12B:
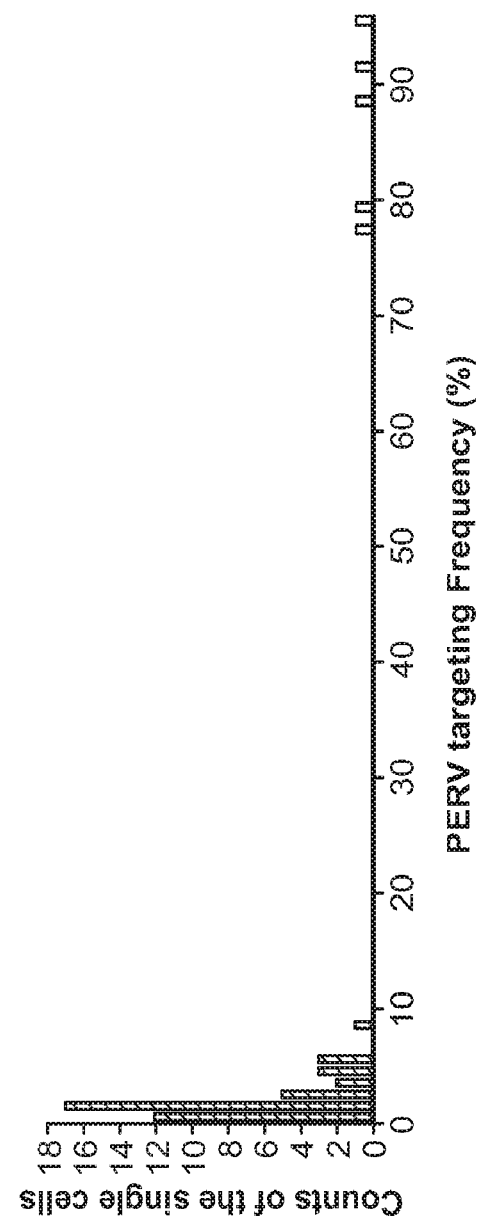

Initial experiments showed inefficient PERV editing when Cas9 and the gRNAs were transiently transfected (FIG. 5). Thus a PiggyBac transposon system was used to deliver a doxycycline-inducible Cas9 and the two gRNAs into the genome of PK15 cells (FIGS. 5-6). Continuous induction of Cas9 led to increased targeting frequency of the PERVs (FIG. 8), with a maximum targeting frequency of 37% (~23 PERV copies per genome) observed on day 17 (FIG. 8). Neither higher concentrations of doxycycline or prolonged incubation increased targeting efficiency (FIGS. 7-8), possibly due to the toxicity of non-specific DNA damage by CRISPR-Cas9. Similar trends were observed when Cas9 was delivered using lentiviral constructs (FIG. 9). The cell lines that exhibited maximal PERV targeting efficiencies were genotyped. 455 different insertion and deletion (indel) events centered at the two gRNA target sites (FIG. 2B) was observed. Indel sizes ranged from 1 to 148 bp; 80% of indels were small deletions (<9 bp). The initial deep sequencing results was validated with Sanger Sequencing (FIG. 10).

Figure 2B:
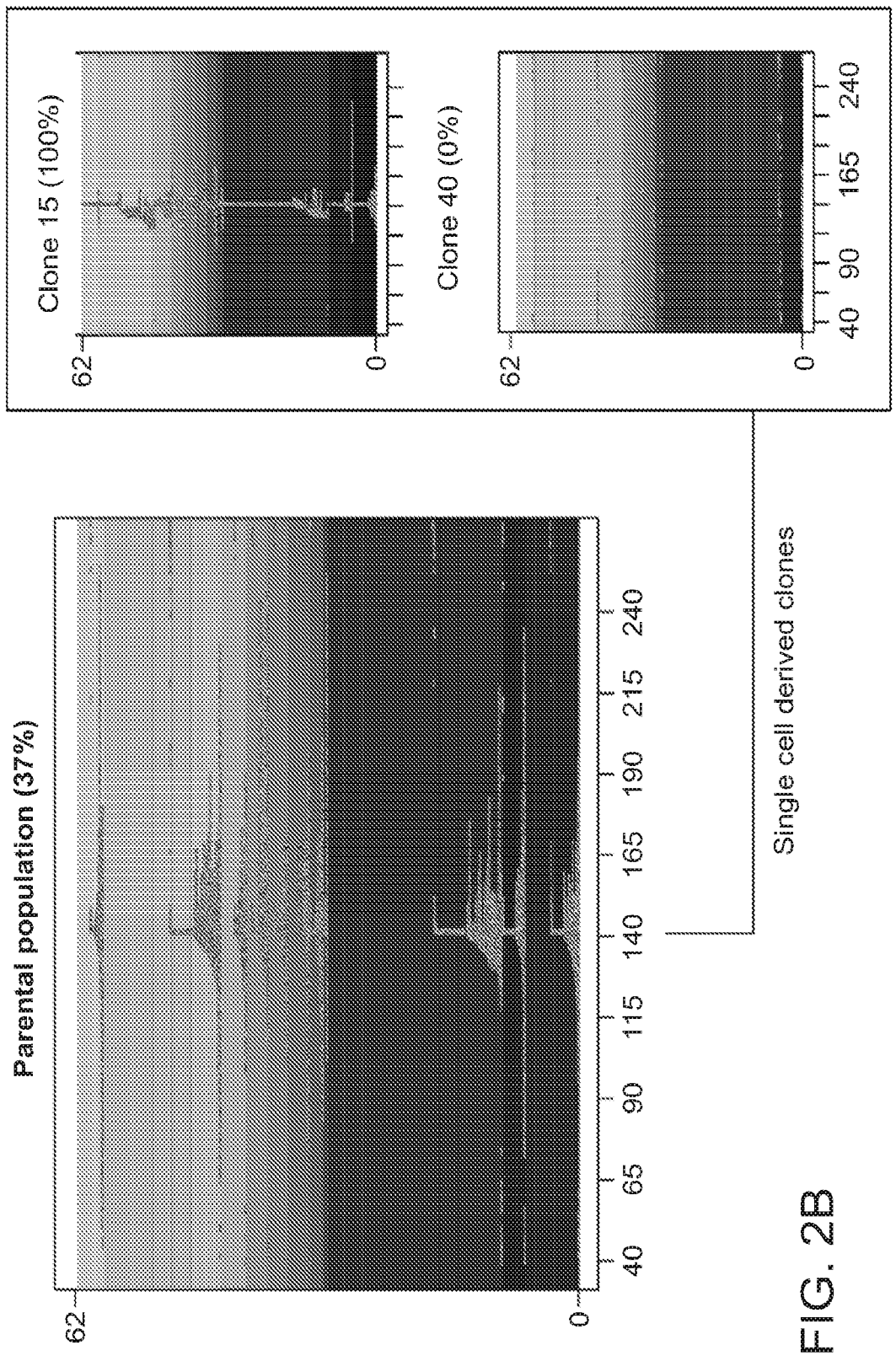
Figure 13:
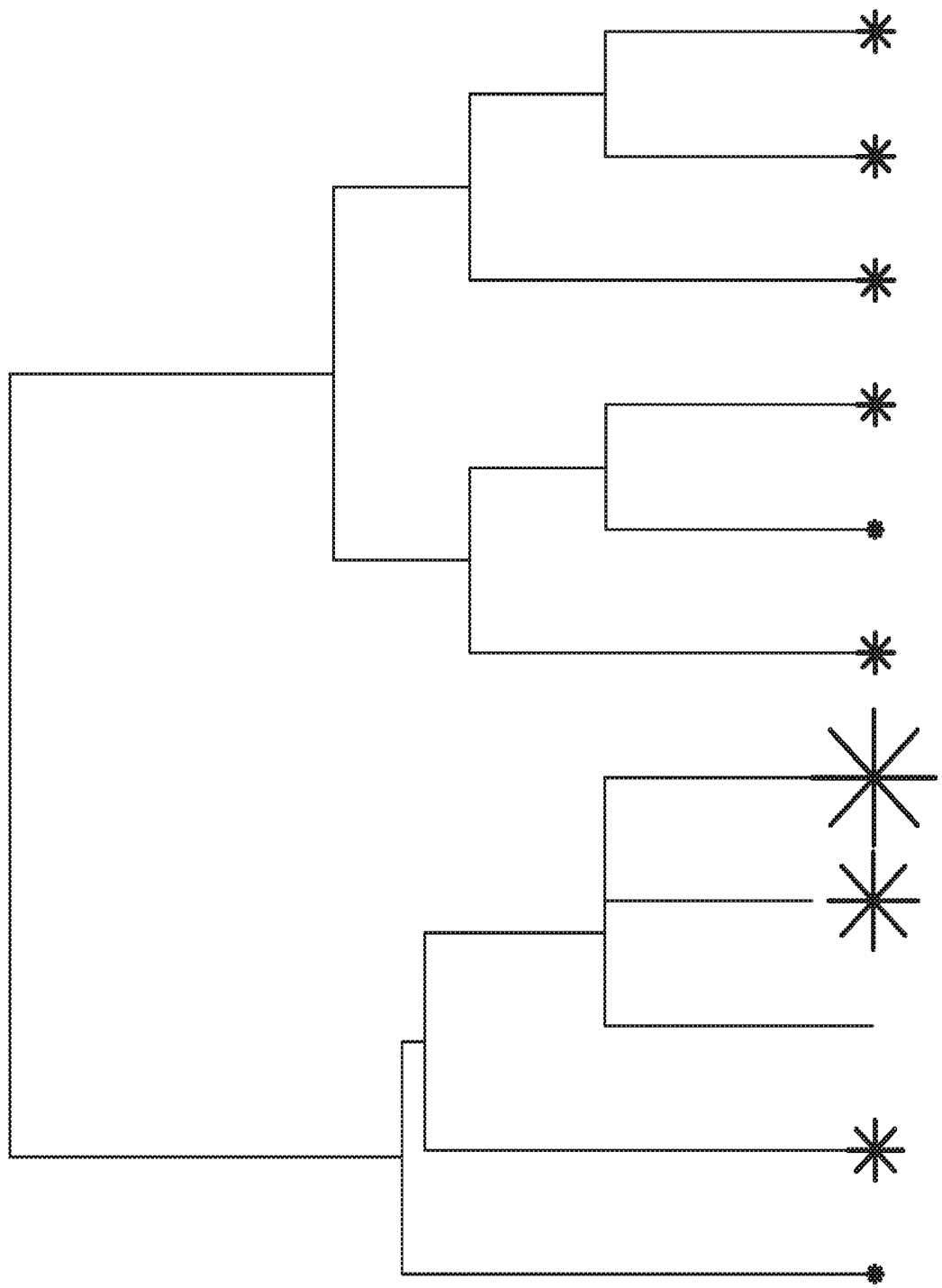
FIG. 13 (S10) illustrates phylogeny of PERV haplotypes.
Figure 14:
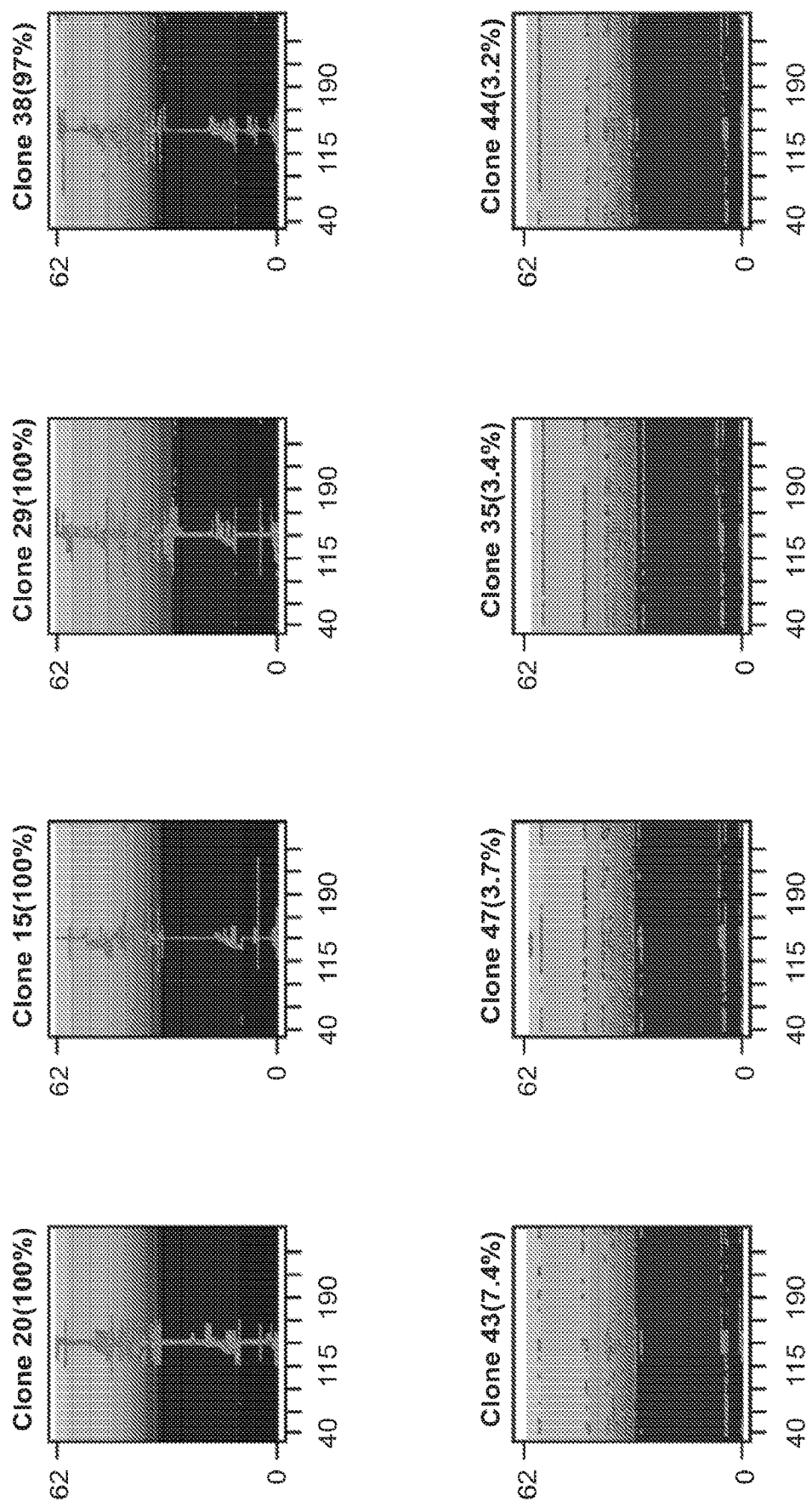
FIG. 14 (S11) illustrates distribution of pol gene disruption.
Figure 14:
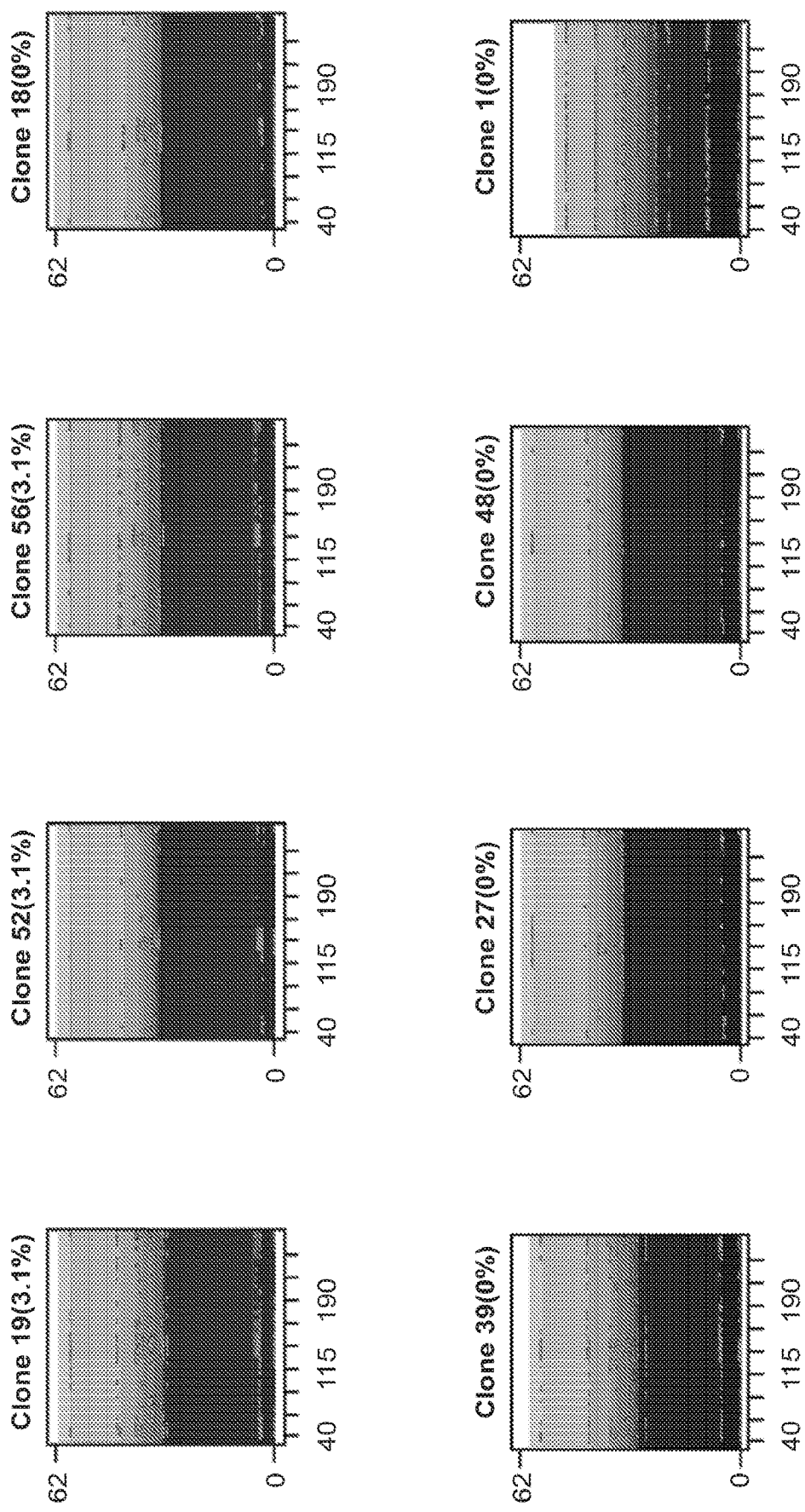
Figure 14:
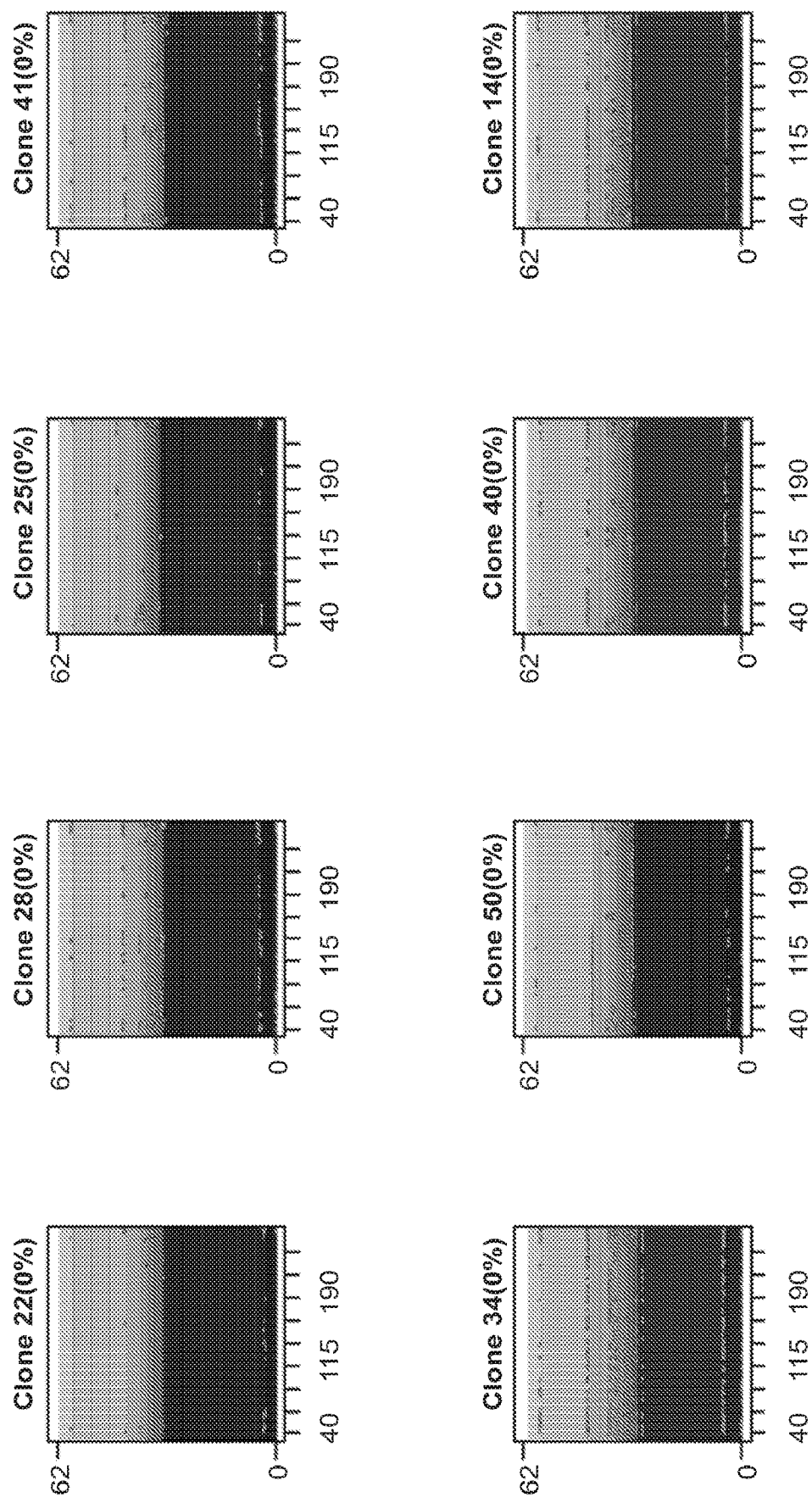
Figure 14:
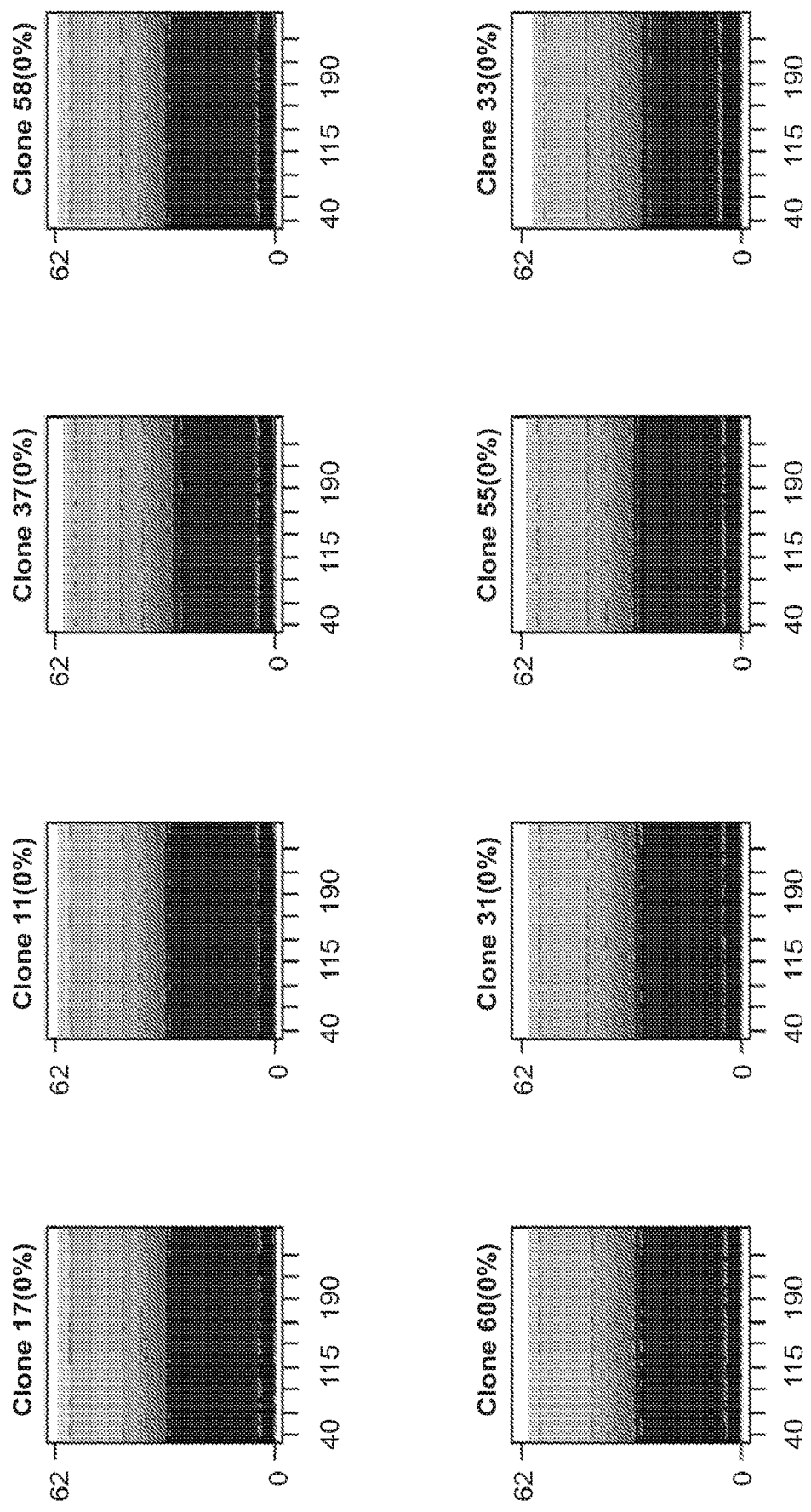
Figure 15A:
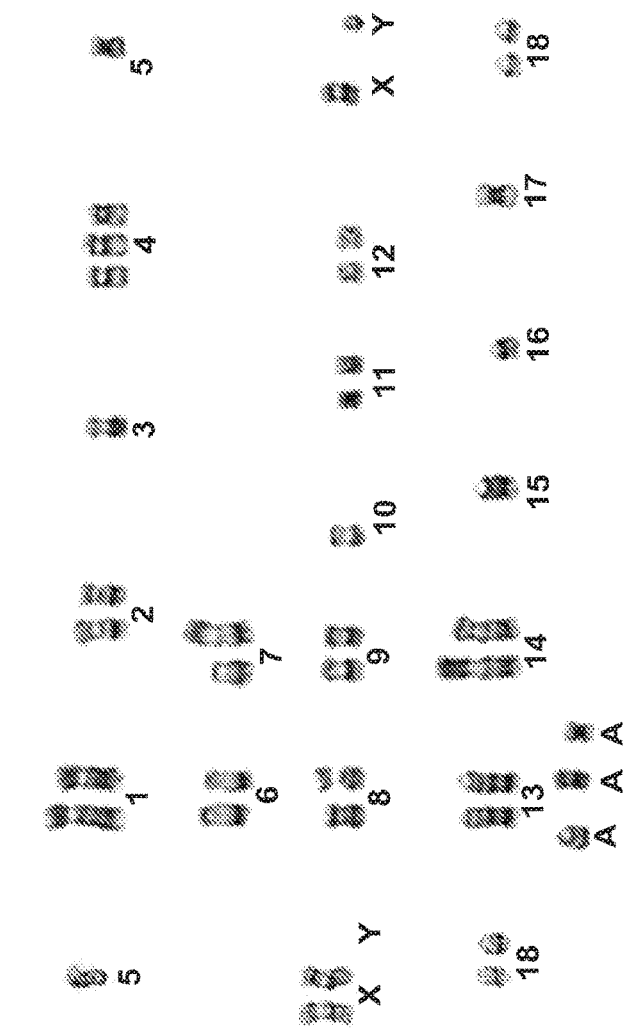
FIGS. 15A-15B (S12) illustrate karyotype analysis of highly and lowly modified PK15 clones.
Figure 15B:
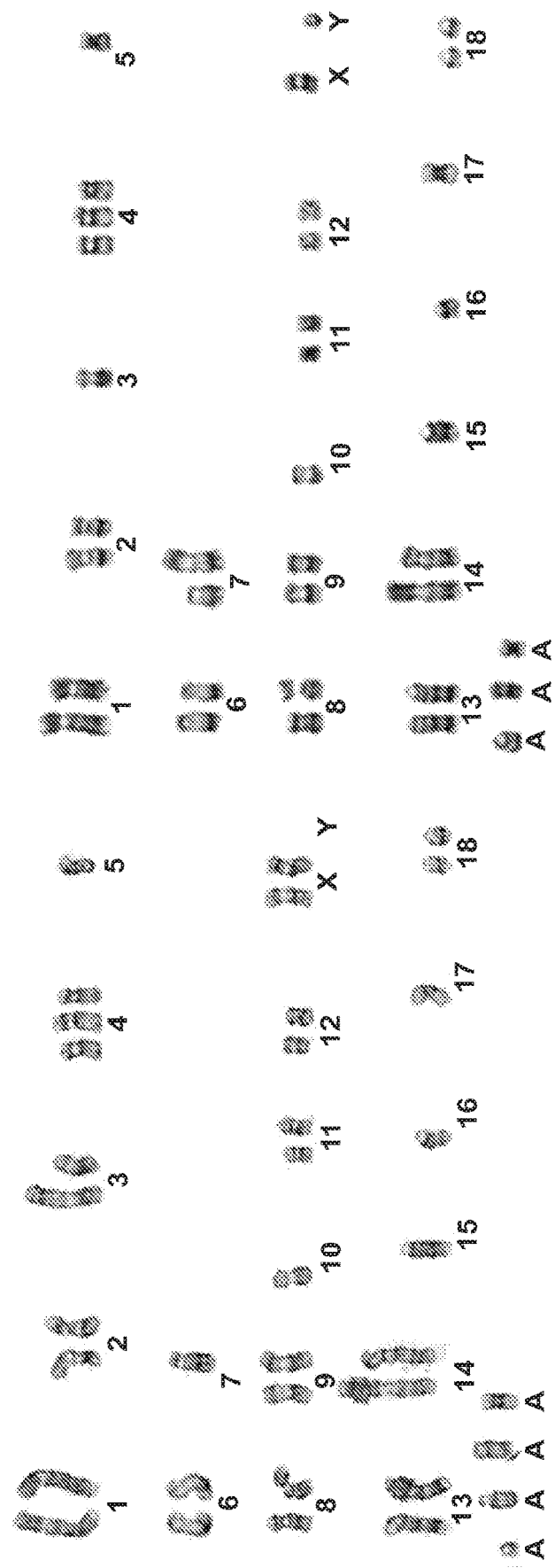
Figure 20A:
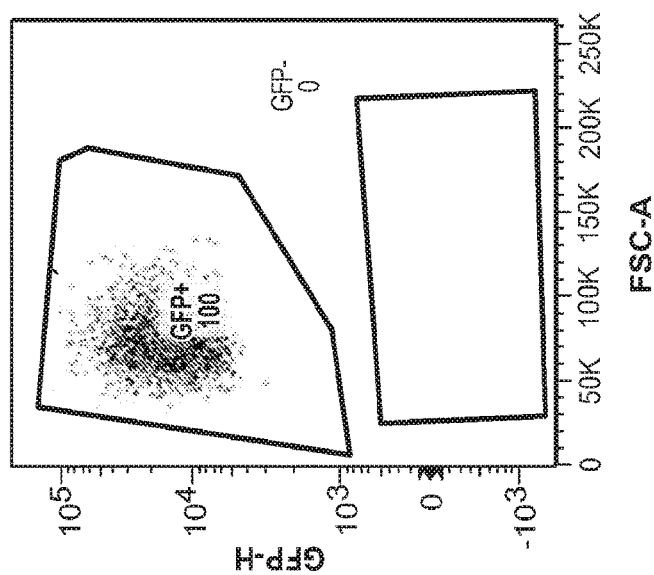
FIGS. 20A-20C (S17) illustrate quality control of the purified HEK293-GFP cells by FACS.
Figure 20B:
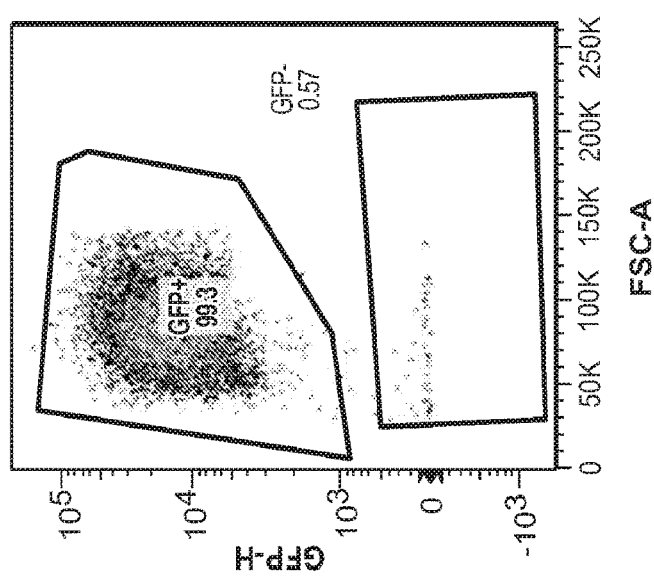
Figure 20C:
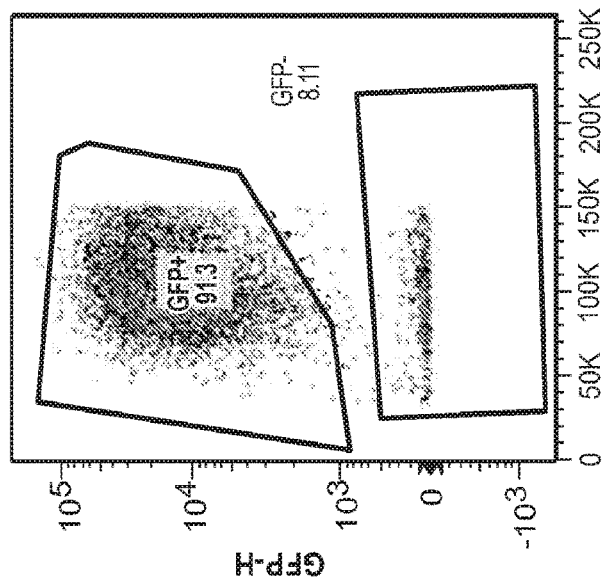
Figure 21A:
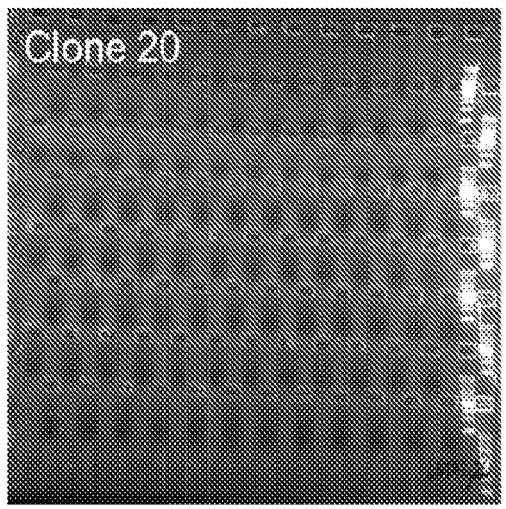
FIGS. 21A-21D (S18) illustrates detection of pig cell contamination in HEK293 cells using pig GGTA1 primers.
Figure 21B:
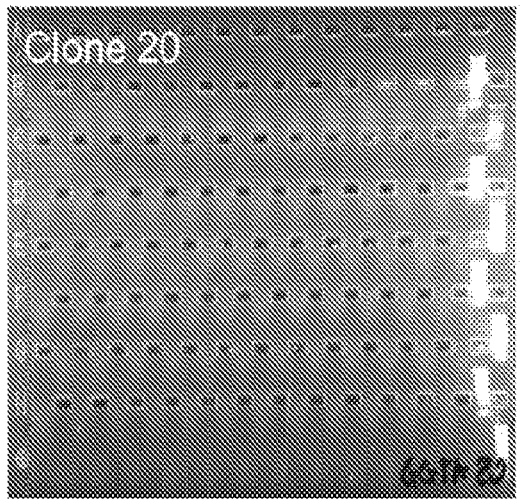
Figure 21C:
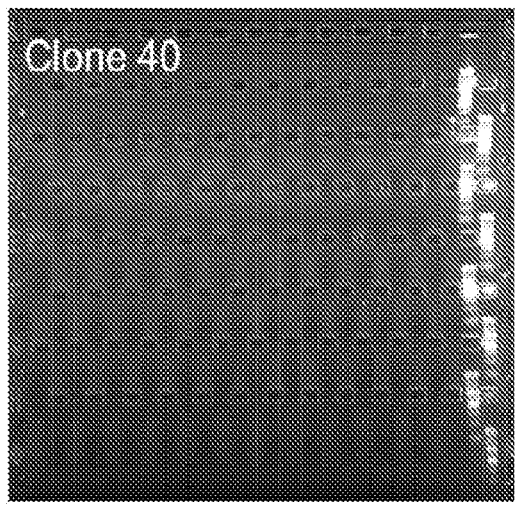
Figure 21D:
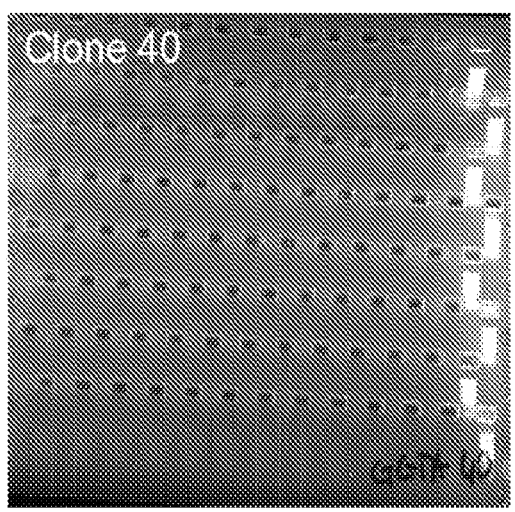
Figure 22A:
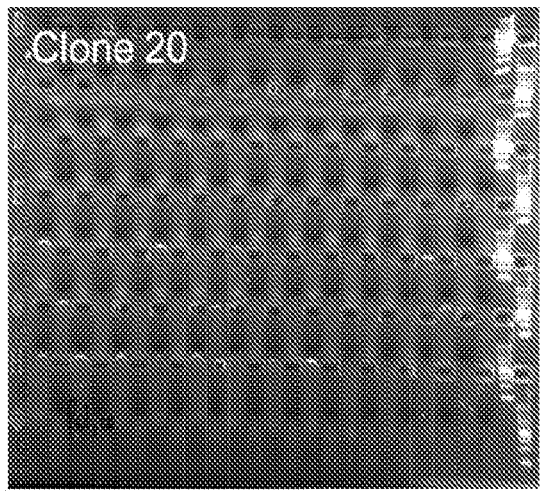
FIGS. 22A-22D (S19) illustrates detection of PERV DNA elements in HEK293 cells using PERV pol primers.
Figure 22B:
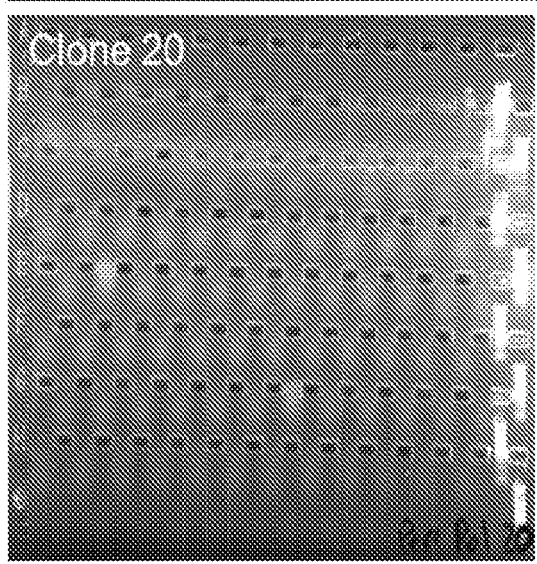
Figure 22C:
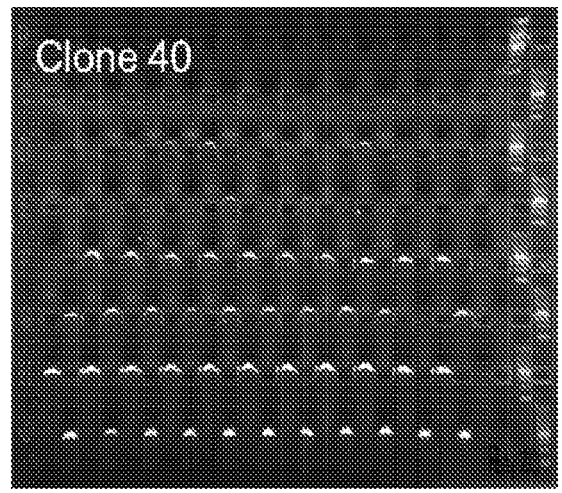
Figure 22D:
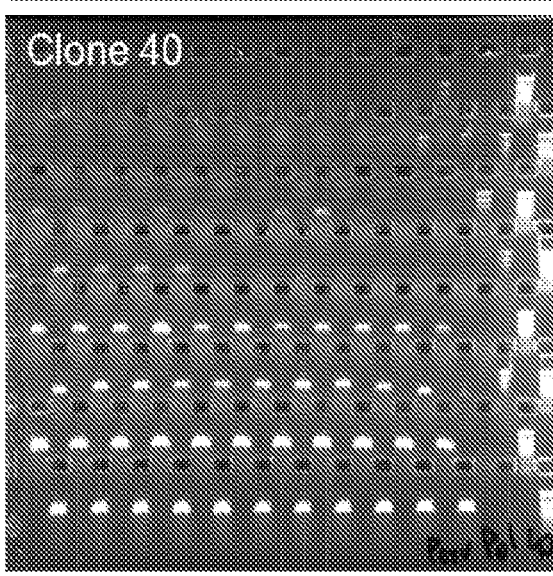
Figure 24A:
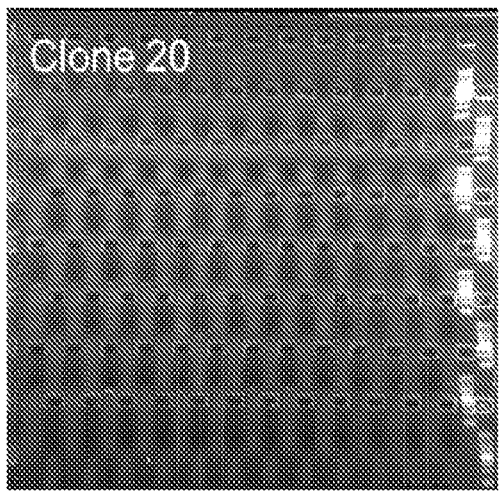
FIGS. 24A-24D (S21) illustrates detection of PERV DNA elements in HEK293 cells using PERV gag primers.
Figure 24B:
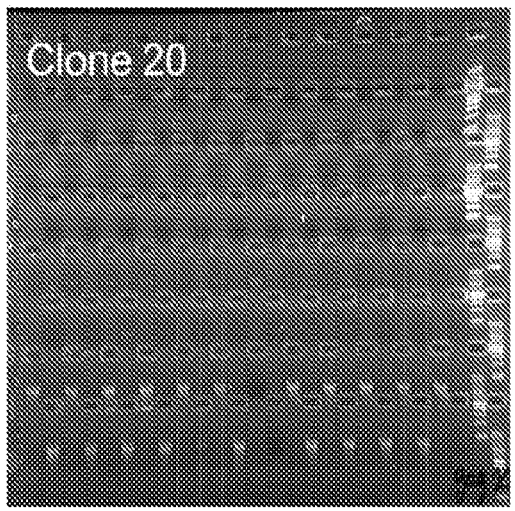
Figure 24C:
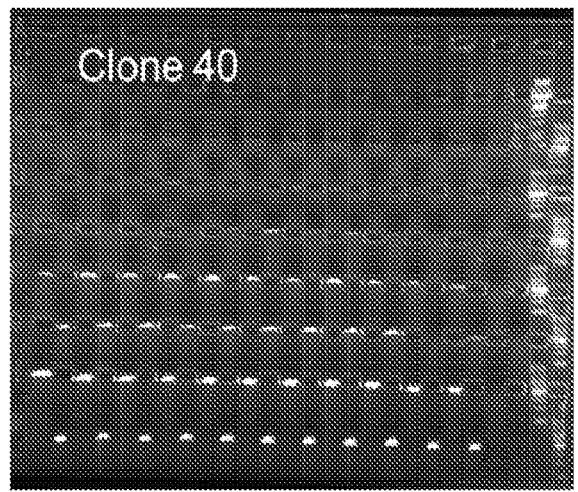
Figure 24D:
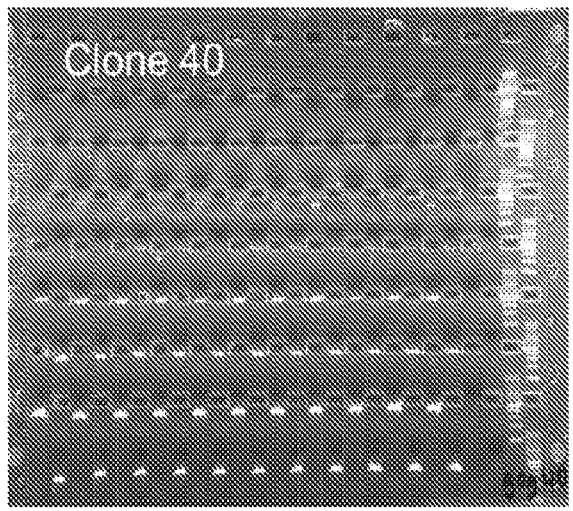
Figures 25A, 25B:
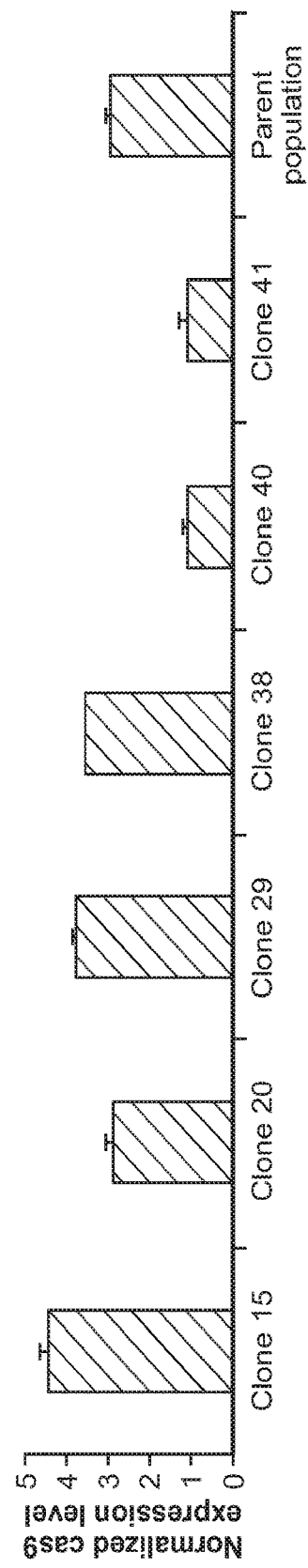
FIGS. 25A-25B (S22) illustrates Cas9/2gRNAs expression levels in highly and lowly modified clones.
Figure 26:
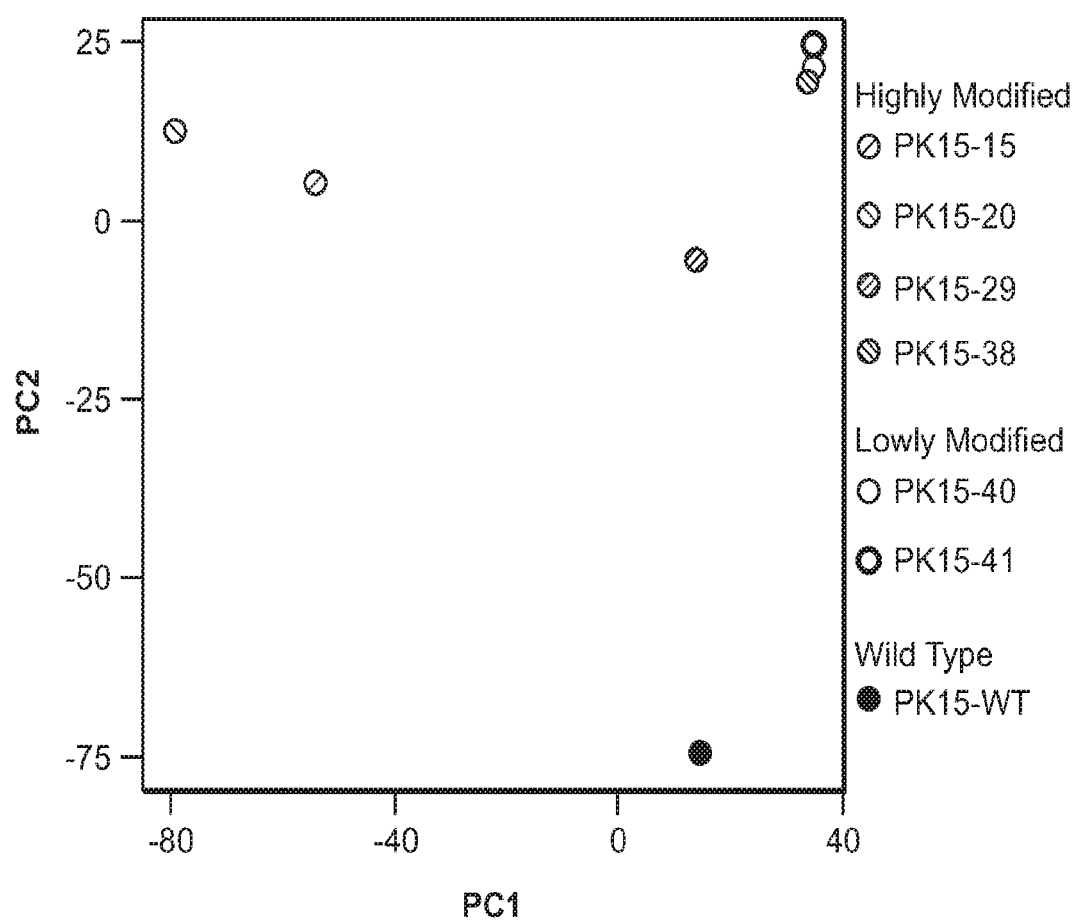
FIG. 26 (S23) illustrates principle component analysis of highly and lowly modified PK15 clones.
Figure 27A:
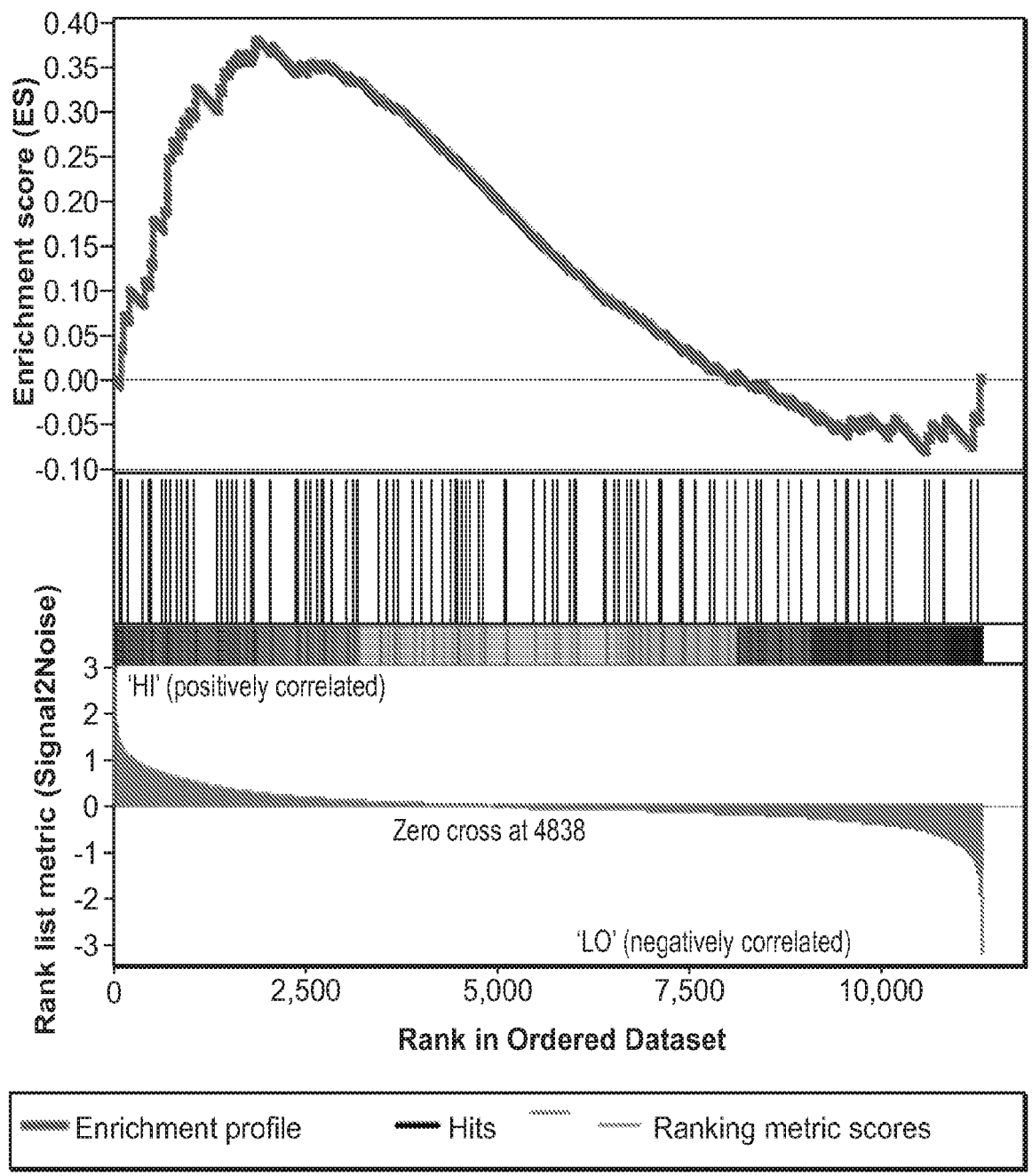
Figure 28:
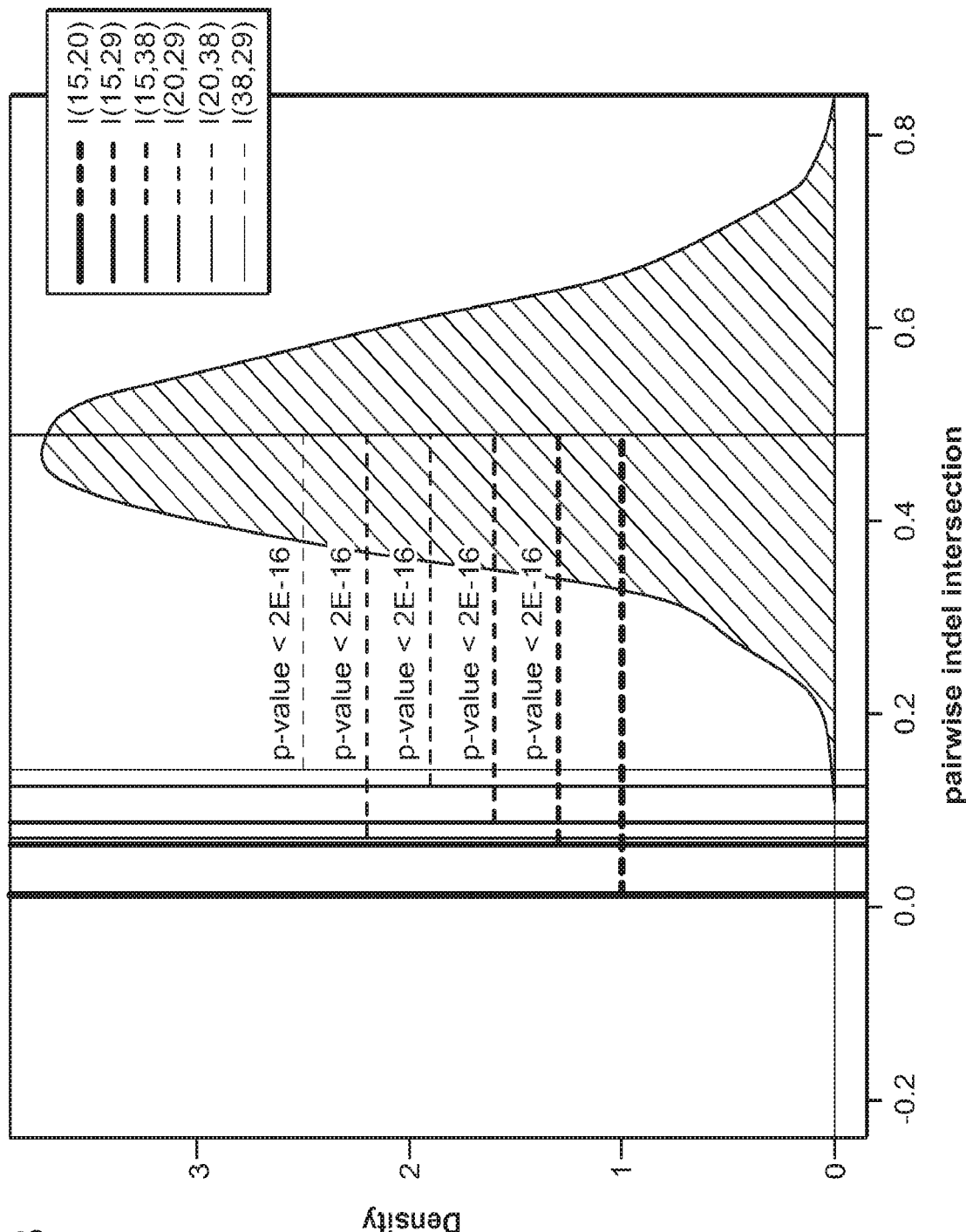
FIG. 28 (S25) illustrates indel composition analysis and comparison among highly modified clones.

Single cells from PK15 cells with high PERV targeting efficiency were sorted using flow cytometry and genotyped the pol locus of the resulting clones via deep sequencing. A repeatable bimodal (FIG. 2A, FIG. 11, and FIGS. 12A-12B) distribution was observed with ~10% of the clones exhibiting high levels of PERV disruption (97%-100%), and the remaining clones exhibiting low levels of editing (<10%). Individual indel events were examined in the genomes of these clones (FIG. 2B, FIG. 13, and FIG. 14). For the highly edited clones (Clone 20, 100%; Clone 15, 100%; Clone 29, 100%; Clone 38, 97.37%), only 16-20 unique indel patterns in each clone (FIG. 2B, FIG. 14) were observed. In addition, there was a much higher degree of repetition of indels within each clone than across the clones (FIG. 28), suggesting a mechanism of gene conversion in which previously mutated PERV copies were used as templates to repair wild-type PERVs cleaved by Cas9 (FIG. 2B, FIG. 28). Mathematical modeling of DNA repair during PERV elimination (FIGS. 29A-29D) and analysis of expression data (FIGS. 25A-25B, FIG. 26, and FIG. 27A-27B) supported this hypothesis and suggested that highly edited clones were derived from cells in which Cas9 and the gRNAs were highly expressed.

Figure 30:
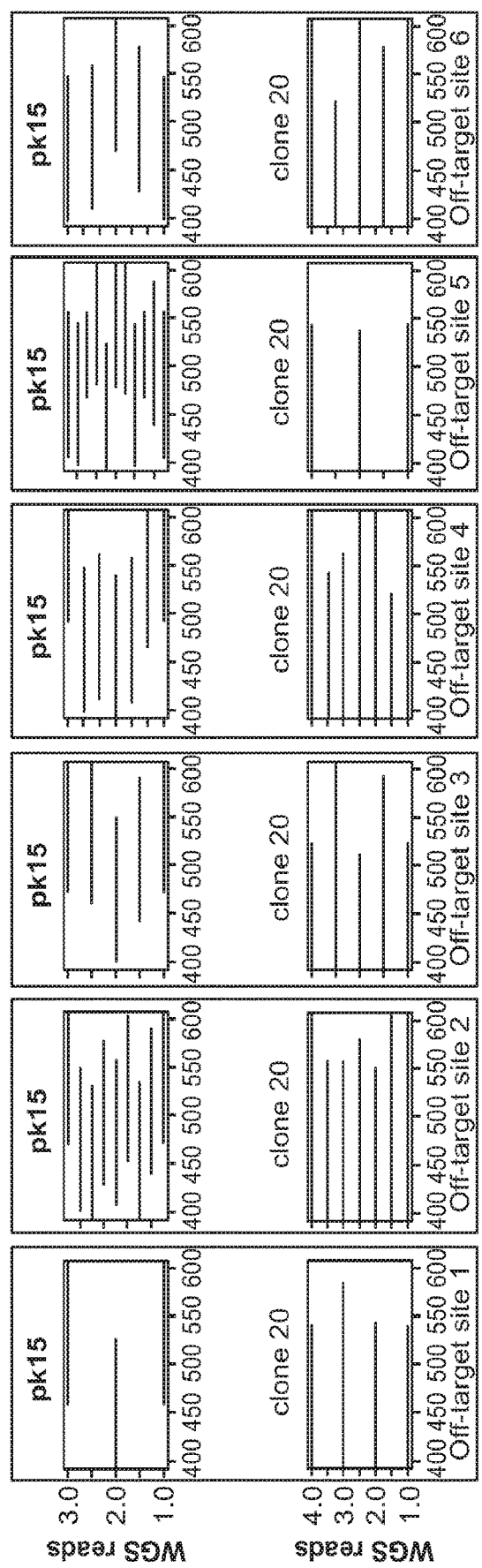
FIG. 30 (S27) illustrates off-target analysis using Whole Genome Sequencing (WGS).
Figure 30:
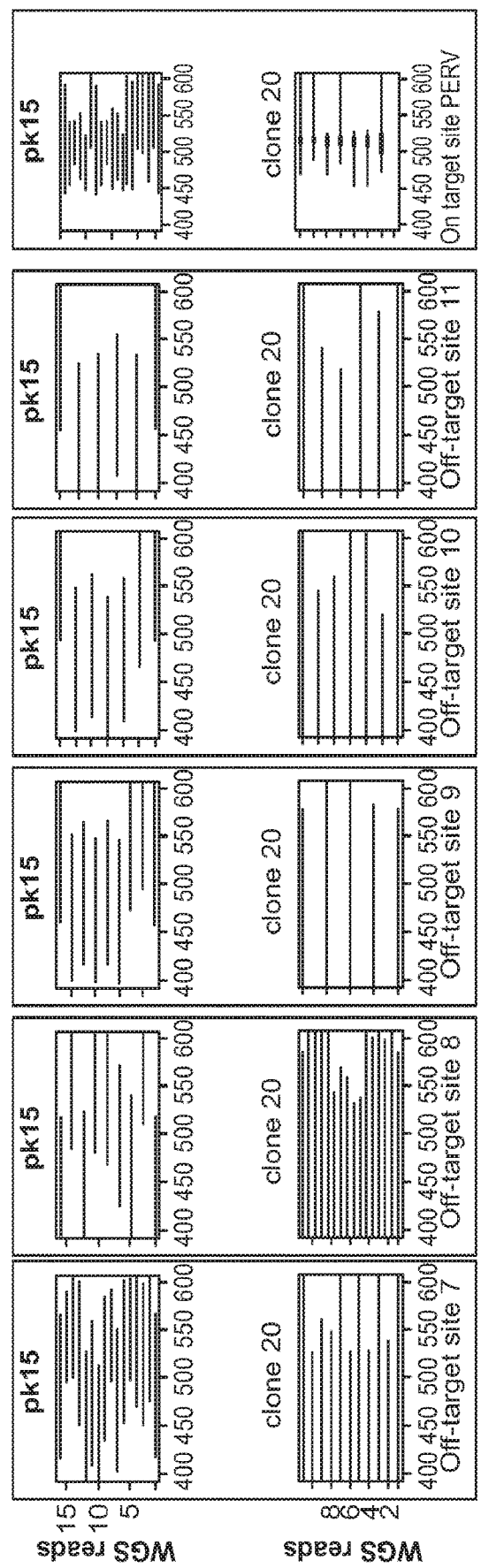

Next, unexpected genomic rearrangements had occurred as a result of the multiplexed genome editing was examined. Karyotyping of individual modified clones (FIGS. 15A-15B, FIG. 16, and FIG. 17) indicated that there were no observable genomic rearrangements. 11 independent genomic loci with at most 2 bp mismatches to each of the intended gRNA targets were examined and observed no non-specific mutations (FIG. 30). This suggests that our multiplexed Cas9-based genome engineering strategy did not cause catastrophic genomic instability.

Figure 3A:
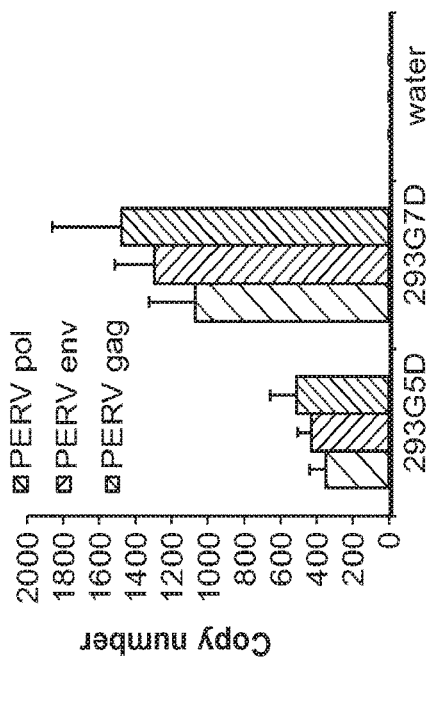
FIGS. 3A-3D illustrate: (A) Detection of PERV pol, gag, and env DNA in the genomes of HEK-293-GFP cells after co-culturing with PK15 cells for 5 days and 7 days (293G5D and 393G7D, respectively). A pig GGTA1 primer set was used to detect pig cell contamination of the purified human cells. (B) qPCR quantification of the number of PERV elements in 1000 293G cells derived from a population co-cultured with wild type PK15 cells using specific primer sets. (N=3, mean+/−SEM) (C) qPCR quantification of the number of PERV elements in PK15 Clones 15, 20, 29, and 38, with high levels of PERV pol modification, and minimally modified Clones 40 and 41. (N=3, mean+/−SEM) (D) Results of PCR on PERV pol on genomic DNA from various numbers of HEK 293-GFP cells (0.1, 1, 10, and 100) isolated from populations previously cultured with highly modified PK15 Clone 20 and minimally modified Clone 40. See FIGS. 21A-21D, FIGS. 22A-22D, FIGS 23A-23D and FIGS. 24A-24D for a full panel of PCR reactions.
Figure 3B:
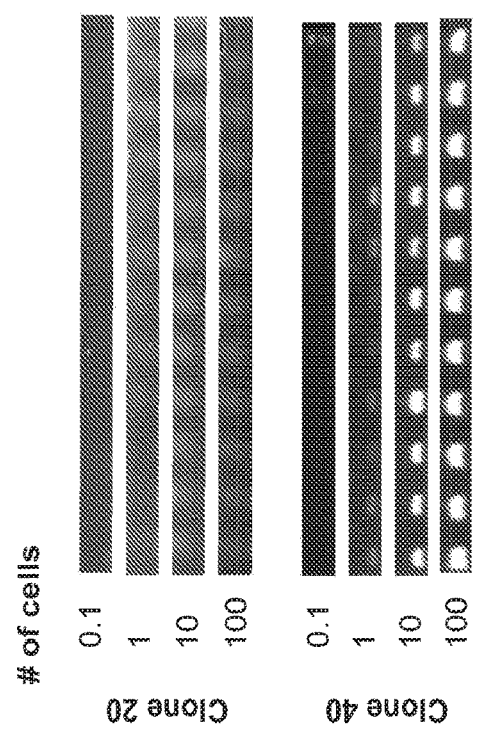
Figure 3C:
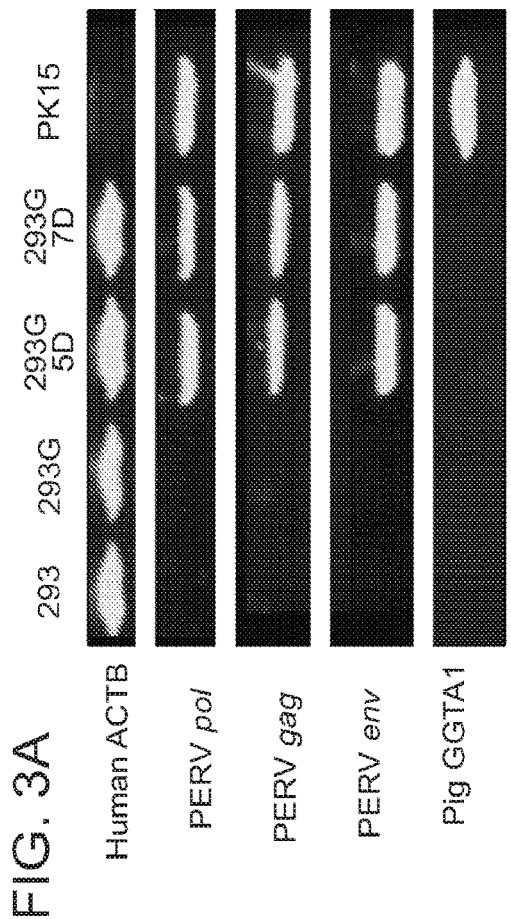
Figure 3D:
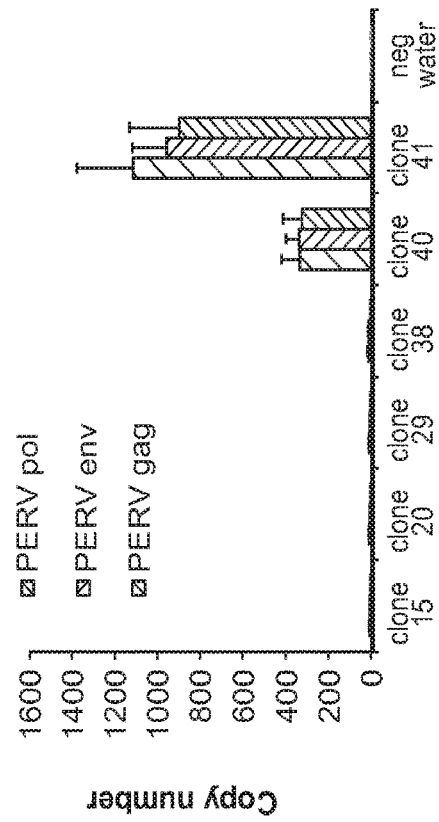

Last, disruption of all copies of PERV pol in the pig genome could eliminate in vitro transmission of PERVs from pig to human cells was examined. No detection of RT activity in the cell culture supernatant of the highly modified PK15 clones (FIG. 18) was observed, suggesting that modified cells only produced minimal amounts of PERV particles. Co-culture of WT and highly modified PK15 cells with HEK 293 cells were tested directly for transmission of PERV DNA to human cells. After co-culturing PK15 WT and HEK 293 cells for 5 days and 7 days (FIG. 19, FIGS. 20A-20C), PERV pol, gag, and env sequences in the HEK 293 cells were detected (FIG. 3A). The estimated frequency of PERV infection was approximately 1000 PERVs/1000 human cells (FIG. 3B). However, PK15 clones with >97% PERV pol targeting exhibited up to 1000-fold reduction of PERV infection, similar to background levels (FIG. 3C). These results were validated with PCR amplification of serial dilutions of HEK293 cells that had a history of contact with PK15 clones (FIG. 3D, FIGS. 21A-21D, FIGS. 22A-22D, FIGS. 23A-23D and FIGS. 24A-24D). PERVs in single HEK293 cells isolated from the population co-cultured with minimally modified Clone 40 was consistently detected, but could not distinctly detect PERVs in 100 human cells from the population co-cultured with highly modified Clone 20. Thus, PERV infectivity of the engineered PK15 cells had been reduced by up to 1000 fold.

In summary, it was successfully targeted the 62 copies of PERV pol in PK15 cells and demonstrated greatly reduced in vitro transmission of PERVs to human cells. While in vivo PERV transmission to humans has not been demonstrated, PERVs are still considered risky and our strategy could completely eliminate this. As no porcine embryonic stem cells exist, this system will need to be recapitulated in primary porcine cells and cloned into animals using somatic cell nuclear transfer. Moreover, simultaneous Cas9 targeting of 62 loci in single pig cells without salient genomic rearrangement was achieved. To our knowledge, the maximum number of genomic sites previously reported to be simultaneously edited has been six. Our methods thus open the possibility of editing other repetitive regions of biological significance.

Example 2. Methods

PERV copy number quantification: Droplet Digital PCR™ PCR (ddPCR™) was usd to quantify the copy number of PERVs according to the manufacturer's instructions (Bio-Rad). Briefly, genomic DNA (DNeasy Blood & Tissue Kit, Qiagen) from cultured cells was purified, digested 50 ng genomic DNA with MseI (10 U) at 37° C. for 1 hour, and prepared the ddPCR reaction with 10 µl 2× ddPCR Master mix, 1 µl of 18 µM target primers & 5 µM target probe (VIC), 10 of 18 µM reference primers & 5 µM reference probe (FAM), 5 ng digested DNA, and water to total volume of 20 µl. The sequence of the primers and the probe information can be found in Extended Data Table 1.

Methods

TABLE 1

Primers used in ddPCR assay

| Name | Sequence |
| --- | --- |
| PrimerPol1-FW | CGACTGCCCCAAGGGTTCAA (SEQ ID NO: 1) |
| PrimerPol2-FW | CCGACTGCCCCAAGAGTTCAA (SEQ ID NO: 2) |
| PrimerPol-RV | TCTCTCCTGCAAATCTGGGCC (SEQ ID NO: 3) |
| ProbePol | /56FAM/CACGTACTGGAGGAGGGTCACCTG (SEQ ID NO: 4) |
| Primerpig_actin_F | Taaccgatcctttcaagcattt (SEQ ID NO: 5) |
| Primerpig_actin_R | Tggtttcaaagcttgcatcata (SEQ ID NO: 6) |
| Probepig_actin | /5Hex/cgtggggatgcttcctgagaaag (SEQ ID NO: 7) |
| Primerpig_GAPDH_F | Ccgcgatctaatgttctctttc (SEQ ID NO: 8) |
| Primerpig_GAPDH_R | Ttcactccgaccttcaccat (SEQ ID NO: 9) |
| Probepig_GAPDH | /5Hex/cagccgcgtccctgagacac (SEQ ID NO: 10) |

CRISPR-Cas9 gRNAs design: MUSCLE was used to carry out a multiple sequence alignment of 245 endogenous retrovirus found in the porcine genome. A phylogenetic tree of the sequences was built and identified a clade that included the PERVs (see FIG. 1a). The R library DECIPHER was used to design specific gRNAs that target all PERVs but no other endogenous retroviral sequences.

Cell culture: PK15 were maintained in Dulbecco's modified Eagle's medium (DMEM, Invitrogen) high glucose supplemented with 10% fetal bovine serum (Invitrogen), and 1% penicillin/streptomycin (Pen/Strep, Invitrogen). All cells were maintained in a humidified incubator at 37° C. and 5% $CO_2$.

PiggyBac-Cas9/2gRNAs construction and cell line establishment: PiggyBac-Cas9/2gRNAs construct is derived from a plasmid previously reported in Wang et al (2). Briefly, a DNA fragment encoding U6-gRNA1-U6-gRNA2 was synthesized (Genewiz) and incorporated it into a PiggBac-Cas9 construct. To establish PK15 cell lines with PiggyBac-Cas9/2gRNAs integration, $5·10^5$ PK15 cells was transfected with 4 μg PiggyBac-Cas9/2gRNAs plasmid and 1 μg Super PiggyBac Transposase plasmid (System Biosciences) using Lipofectamine 2000 (Invitrogen). To enrich for the cells carrying the integrated construct, 2 μg/mL puromycin was added to the transfected cells. Based on the negative control, puromycin was applied to wild type PK15 cells, it was determined that the selection completed in 3 days. The PK15-PiggyBac cell lines were maintained with 2 μg/mL puromycin hereafter. 2 μg/ml doxycycline was applied to induce Cas9 expression.

Lentivirus-Cas9/2gRNAs construction and cell line establishment: Lenti-Cas9/2gRNAs constructs were derived from a plasmid previously reported (3). A DNA fragment encoding U6-gRNA1-U6-gRNA2 was synthesized (Genewiz) and incorporated it into a Lenti-Cas9-V2. To generate lentivirus carrying Lenti-Cas9/2gRNAs, $~5·10^6$ 293 FT HEK cells was transfected with 3 μg Lenti-Cas9-gRNAs and 12 μg ViraPower Lentiviral Packaging Mix (Invitrogen) using Lipofectamine 2000. The lentiviral particles were collected 72 hours after transfection, and the viral titer was measured using Lenti-X GoStix (Takara Clonetech). $~10^5$ lentiviral particles to $~1·10^6$ PK15 cells were transduced and conducted selection by puromycin to enrich transduced cells 5 days after transduction. The PK15-Lenti cell lines were maintained with 2 μg/mL puromycin thereafter.

Genotyping of colonized and single PK15 cells: PK15 cultures were dissociated using TrypLE (Invitrogen) and resuspended in PK15 medium with the viability dye ToPro-3 (Invitrogen) at a concentration of $1-2·10^5$ cells/ml. Live PK15 cells were single-cell sorted using a BD FACSAria II SORP UV (BD Biosciences) with 100 mm nozzle under sterile conditions. SSC-H versus SSC-W and FSC-H versus FSC-W doublet discrimination gates and a stringent '0/32/16 single-cell' sorting mask were used to ensure that one and only one cell was sorted per well. Cells were sorted in 96-well plates with each well containing 1000 μl PK15 medium. After sorting, plates were centrifuged at 70 g for 3 min. Colony formation was seen 7 days after sorting and genotyping experiment was performed 2 weeks after FACS.

To genotype single PK15 cells without clonal expansion, the PERV locus was directly amplified from sorted single cells according to a previously reported single cell genotyping protocol (4). Briefly, prior to sorting, all plastics and non-biologic buffers were treated with UV radiation for 30 min. Single cells were sorted into 96-well PCR plates with each well carrying 0.5 μl 10×KAPA express extract buffer (KAPA Biosystems), 0.1 μl of 1 U/μl KAPA Express Extract Enzyme and 4.6 μl water. The lysis reaction was incubated at 75° C. for 15 min and inactivated the reaction at 95° C. for 5 min. All reactions were then added to 250 PCR reactions containing 12.5 μl 2×KAPA 2G fast (KAPA Biosystems), 100 nM PERV illumina primers (Methods Table2), and 7.5 μl water. Reactions were incubated at 95° C. for 3 min followed by 25 cycles of 95° C., 10 s; 65° C., 20 s and 72° C., 20 s. To add the Illumina sequence adaptors, 50 of reaction products were then added to 20 μl of PCR mix containing 12.5 ml of 2 KAPA HIFI Hotstart Readymix (KAPA Biosystems), 100 nM primers carrying Illumina sequence adaptors and 7 μl water. Reactions were incubated at 95° C. for 5 min followed by 15-25 cycles of 98° C., 20 s; 65° C., 20 s and 72° C., 20 s. PCR products were checked on EX 2% gels (Invitrogen), followed by the recovery of 300-400 bp products from the gel. These products were then mixed at roughly the same amount, purified (QIAquick Gel Extraction Kit), and sequenced with MiSeq Personal Sequencer (Illumina). Deep sequencing data was analyzed and determined the PERV editing efficiency using CRISPR-GA (5).

TABLE 2

Primers used in the PERV pol genotyping

| Name | Sequence |
| --- | --- |
| illumina_primerPol1 | ACACTCTTTCCCTACACGACGCTCTTCCGATCTCGACTGCCCC AAGGGTTCAA (SEQ ID NO: 11) |
| illumina_primerPol2 | ACACTCTTTCCCTACACGACGCTCTTCCGATCTCCGACTGCCC CAAGAGTTCAA (SEQ ID NO: 12) |
| illumina_primerPo3 | GTGACTGGAGTTCAGACGTGTGCTCTTCCGATCTTCTCTCCTG CAAATCTGGGCC (SEQ ID NO: 13) |

Targeting efficiency estimation: a custom pipeline was built to estimate the efficiency of PERV inactivation. Briefly, the pol gene was amplified and sequenced via Illumina Next Generation Sequencing using PE250 or PE300. First, the two overlapping reads were combined using PEAR (6) and mapped to the reference region using BLAT. After mapping, the reads were grouped into sets containing specific combinations of haplotypes (see Extended Data FIG. 7), and indel types. Read sets with representation lower than 0.5% of the total number of mapped reads were discarded. Finally, the mapping output was parsed to call the different insertions and deletions as described in Güell et al (5).

RNA-seq analysis: The susScr3 pig genome and Ensembl transcripts were obtained from the UCSC Genome Brower Database. RNA-Seq reads were mapped to the reference genome using the STAR software (7) and the RPKM of the transcripts were quantified using BEDTools (8). Differential expression analysis was performed in R using the DESeq2 package (9), and gene set enrichment analysis was carried out by the GSEA software (10), with gene set definitions obtained from the software's website.

Reverse transcriptase (RT) assay: To test the RT activity of the PK15 cells and modified PK15 clones (4 highly and 1 lowly modified clones), $5 \cdot 10^5$ cells were plated in T75 cm² flasks, and collected the supernatant 4 days after seeding. The media was filtered using a 0.45 µM Millex-HV Syringe Filter (EMD Millipore Corporation), and the filtered supernatant was concentrated at 4000 g for 30 min using Amicon Ultra-15 Centrifugal Filter Unit (EMD Millipore Corporation). The concentrated supernatant was ultra-centrifuged at 50,000 rpm for 60 min. The supernatant was carefully removed, and the virus pellet was collected and lysed with 20 µl of 10% NP40 at 37° C. for 60 min.

The RT reaction was conducted using the Omniscript RT Kit (Qiagen). The total volume of the reaction was 20 µl, which contained 1 □ RT buffer, 0.5 mM dNTPs, 0.5 µM Influenza reverse primer (5' CTGCATGACCAGGGTT-TATG 3') (SEQ ID NO:14), 100 units of RnaseOUT (Life Technology, Invitrogen), 100 units of SuperRnase Inhibitor (Life Technologies), 5 µl of sample lysis and 40 ng of IDT-synthesized Influenza RNA template which was rnase resistant in both 5' and 3' end. The RNA template sequence was 5' rA*rA*rC*rA*rU*rGrGrArArCrCrUrUr-UrGrGrCrCrCrUrGrUrUrCrArUrUrUrUrArGrArAr ArUr-CrArArGrUrCrArArGrArUrArCrGrCrArGrArArGrAr-GrUrArGrArCrArUrArArArArCrCr CrUrGrGrUrCrArUrGrCrArGrArCrCrU*rC*rA*rG*rU*rG 3' (* phosphodiester bond) (SEQ ID NO:15). After the RT reaction was completed, the RT product was examined by PCR using Influenza forward (5' ACCTTTGGCCCTGTT-CATTT 3') (SEQ ID NO:16) and Influenza reverse primers (sequence shown as above). The expected size of the amplicon was 72 bp.

Infectivity Assay

HEK293-GFP cell line establishment: The Lenti-GFP construct was derived from the plasmid pLVX-IRES-Zs-Green1 (Clontech. Catalog No. 632187; PT4064-5). To generate the lentivirus carrying Lenti-GFP, ~$5 \cdot 10^6$ 293 FT HEK cells were transfected with 3 µg of pVX-ZsGreen plasmid and 12 µg of ViraPower Lentiviral Packaging Mix (Invitrogen) using Lipofectamine 2000 (Invitrogen). Lentiviral particles were collected 72 hours after transfection, and the viral titer was measured using Lenti-X GoStix (Takara Clonetech). ~$10^5$ lentivirus particles to ~$1 \cdot 10^6$ HEK293 cells were transfected and conducted selection by puromycin to enrich the transduced cells 5 days after transduction. The 293-GFP-Lenti cell lines were maintained with 0.5 µg/mL puromycin thereafter.

Infectivity test of PK15 WT to HEK293-GFP: $1 \cdot 10^5$ cells of Lenti-GFP-293FT HEK cells and $1 \cdot 10^5$ PK15 WT cells were cultured together in a 6-well plate. In parallel, $2 \cdot 10^5$ PK15 WT cells were cultured alone in another well as a control. The puromycin selection experiment was done by adding 5 µg/ml of the antibiotic for 7 days. The time point was determined when no viable cells in the control well and approximately 100% GFP positive cells in the experimental well as the time point when the puromycin selection was completed to purify lenti-GFP-293FT human cells. Cells from the 293FT HEK/PK15 WT co-culture were collected at different time periods. The genomic DNA was extracted using (DNeasy Blood & Tissue Kit, Qiagen) from cultured cells of the 293-GFP WT, PK15 WT and the co-cultured cells. The genomic DNA concentration was measured using a Qubit 2.0 Fluorometer (Invitrogen), and 3 ng from each sample was used as DNA template for PCR. In all, 1 µL of the genomic DNA were added to 25 µL of a PCR mix containing 12.5 µL 2× KAPA Hifi Hotstart Readymix (KAPA Biosystems) and 100 µM of primers as listed in Methods Table 3. Reactions were incubated at 95° C. for 5 min followed by 35 cycles of 98° C., 20 s; 65° C., 20 s and 72° C., 20 s. PCR products were visualized on EX 2% gels (Invitrogen) and observed for bands of 300-400 base pairs.

TABLE 3

A table exhibiting the primers used in the infectivity assay

| Name | Sequence |
| --- | --- |
| PERV pol-Forward | GGG AGT GGG ACG GGT AAC CCA (SEQ ID NO: 17) |
| PERV pol-Reverse | GCC CAG GCT TGG GGA AAC TG (SEQ ID NO: 18) |
| PERV env-Forward | ACC TCT TCT TGT TGG CTT TG (SEQ ID NO: 19) |
| PERV env-Reverse | CAA AGG TGT TGG TGG GAT GG (SEQ ID NO: 20) |
| PERV gag-Forward | CGC ACA CTG GTC CTT GTC GAG (SEQ ID NO: 21) |
| PERV gag-Reverse | TGA TCT AGT GAG AGA GGC AGA G (SEQ ID NO: 22) |
| Pig GGTA1-Forward | GGA GCC CTT AGG GAC CAT TA (SEQ ID NO: 23) |
| Pig GGTA1-Reverse | GCG CTA AGG AGT GCG TTC TA (SEQ ID NO: 24) |
| Human ACTB-Forward | GCC TTC CTT CCT GGG CAT GG (SEQ ID NO: 25) |
| Human ACTB-Reverse | GAG TAC TTG CGC TCA GGA GG (SEQ ID NO :26) |

Quantification of PERV copy numbers infected in HEK293-GFP cells: qPCR was performed to quantify the PERV copy number in HEK293-GFP cells. Genomic DNA of PK15 WT cells of different amounts was used as the template for the qPCR reactions. Reactions were conducted in triplicate using KAPA SYBR FAST qPCR Master Mix Universal (KAPA Biosystems). PERV pol, env, gag primers, human ACTB and pig GGTA1 primers (Methods Table 3) were added to a final concentration of 1 µM. Reactions were incubated at 95° C. for 3 min (enzyme activation) followed by 50 cycles of 95° C., 5 s (denaturation); 60° C., 60 s (annealing/extension). The logarithm of the genomic DNA amount linearizes with the quantification cycle (Cq). pol, gag, env primers were used to examine for presence of PERVs. Pig GGTA1 primers served to control for potential porcine genome contaminants in human cells after infection. All experiments were conducted in triplicate.

Infectivity Assay of the Modified PK15 clones to HEK293-GFP: $1 \cdot 10^5$ cells of HEK293-GFP cells and $1 \cdot 10^5$ cells of the high modified (15, 20, 29, 38) clones and low modified clones (40, 41) were co-cultured in a 6-well plate for 7 days. To isolate the HEK293-GFP cells in order to examine for PERV elements, the GFP positive cells were double sorted to purify the human cell populations.

To quantify the PERV infectivity of different clones to HEK293-GFP cells, both qPCR assays and PCR assays were conducted on series diluted HEK293-GFP cells after sorting. For the qPCR assays, the genomic DNA (DNeasy Blood & Tissue Kit, Qiagen) was extracted from double sorted HEK293-GFP cells. The genomic DNA concentration was measured using Qubit 2.0 fluorometer (Invitrogen). In all, 3 ng of the genomic DNA was added to 20 μL of KAPA SYBR FAST qPCR reaction (KAPA Biosystems) using PERV pol, env, gag and pig GGTA primers respectively (Extended Data Table 2). The qPCR procedure was performed as described above. For the series dilution assay, purified HEK293-GFP cells were sorted (1 cell/well, 10 cells/well, 100 cells/well, 1000 cells/well) into 96-well PCR plates for direct genomic DNA extraction and PCR reactions. Briefly, cells were sorted into 20 μL lysis reaction including 2 μL of 10×KAPA Express Extract Buffer, 0.4 μL of 1 U/μl KAPA Express Extract Enzyme and 17.6 μL of PCR-grade water (KAPA Biosystems). The reactions were then incubated at 55° C. for 10 min (lysis), then at 95° C. for 5 min (enzyme inactivation). Subsequently, the PCR master mix was prepared. In all, 2 μL of the genomic DNA lysis was added to 4 different 25 μL of KAPA Hifi Hotstart PCR reactions (KAPA Biosystems) using 1 μM PERV pol, env, gag primers, and pig GGTA primers, respectively (Extended Data Table 2). The reactions were incubated at 95° C. for 3 min (initial denaturation) followed by 35 cycles of 95° C., 15 s (denaturation); 60° C., 15 s (annealing), 72° C., 15 sec/kb, then 75° C., 1 min/kb (final extension). (KAPA Biosystems). The PCR products were visualized on 96 well E-Gel® Agarose Gels, SYBR® Safe DNA Gel (Invitrogen).

CRISPR-Cas9 off-target analysis: whole genome sequencing (WGS) data was obtained for PK15 (untreated cell line) and clone 20 (highly edited clone). To investigate potential off-target effects of the Cas9/2gRNAs, the reference sequence (Sus Scrofa 10.2) was searched for sites that differed from the 20 bp sequences targeted by the two gRNAs by only 1 or 2 bp. 11 such sites were identified and extracted them, together with 200 bp of their neighboring regions (FIG. 4). BLAT was used to map the WGS reads to the extracted reference sequences and searched for potential indel patterns that had emerged in Clone 20 as a result of off-target effects. An average coverage of 7-8× per loci was obtained. Reads with <50 bp matches with the reference sequence were excluded. In case of reads that mapped to the reference sequence with multiple alignment blocks, which could indicate the presence of indels, reads whose alignment blocks contained <20 bp matches were excluded with the reference sequence. After inspecting the remaining mapped reads, there was no detection any off-target indel patterns present in clone 20. Another challenge was to comprehensive searches for off-targets here is that the Sus Scrofa genome is still neither complete nor completely assembled, limiting the ability to do whole-genome analysis.

Mathematical model of DNA repair process interaction during cumulative PERV inactivation: In this study PERV elements were inactivated by mutations generated by DNA repair processes in response to dsDNA cuts created by Cas9. It is generally understood that dsDNA cuts may be repaired either by non-homologous end joining (NHEJ) or Homologous Repair (HR), and that while HR can create precise copies of a DNA template sequence at the cut site given the presence of a template with suitable homology arms, NHEJ can generate mutations (especially indels) and is often considered "error prone." However, there is also evidence that NHEJ can also repair dsDNA cuts highly accurately (11, 12), and the relative rates of mutated vs. perfect repair by NHEJ have never been precisely measured. Especially when efficient targeted nucleases such as Cas9 are expressed for protracted time periods, perfect repair of a cut site by either NHEJ or HR would regenerate a target site that could be cut again. A plausible hypothesis is that the process of perfect repair and re-cutting would occur repeatedly until a mutation arose that destroyed the nuclease's ability to recognize the target site. To explore the way these repair modalities might work together during the course of PERV elimination, their interactions as a Markov process was modeled. Specifically, it was assumed:

There are N identical copies of the nuclease target in a cell.

Only wild-type targets are recognized and cut, and only one target is cut and repaired at a time.

DNA repair is either
  perfect restoration of the target site by NHEJ (with probability n)
  NHEJ that results in generation of a mutation that ablates target recognition (with probability m)
  repair by HR using any one of the other N−1 target sequences in the cell (with probability h)

Thus, n+m+h=1.

The Markov model computes the probability distribution $P^{(c)}=(p_0^{(c)}, p_1^{(c)}, \ldots, p_N^{(c)})$, where $p_i^{(c)}$ is the probability that there are i target-ablating mutations at cut c, where c=0, 1, 2 . . . . It is assumed that the initial condition $P^{(0)}=(1, 0, \ldots, 0)$, i.e., that all targets begin as wild-type. The N+1-by-N+1 transition matrix M is given as $$\left. \begin{array}{l} M(i, i) = n + h \cdot \dfrac{N-i-1}{N-1} \\ M(i, i+1) = m + h \cdot \dfrac{i}{N-1} \end{array} \right\} \text{ for } 0 \leq i < N$$

$$M(N, N) = 1 \text{ for } i = N$$

$$M(i, j) = 0 \text{ for all other } 0 \leq i, j \leq N$$

Finally, $P^{(c+1)}=P^{(c)}M$ for c=0, 1, 2, . . .

The formulas for M assume proposition ii above and state in mathematical terms that the number of mutated sites in a cell remains unchanged whenever a cut at a wild-type site is repaired perfectly by NHEJ or by HR using another copy of the wild-type template (formula for M(i, i)), but increases by one if the cut is repaired by mutagenic NHEJ or by HR using a previously mutated site (formula for M(i, i+1)).

The model incorporates two notable simplifications to actual biology: (i) Target recognition is assumed to be binary—either the nuclease recognizes a target or it does not. This is tantamount to assuming that small mutations that still support target recognition do not substantially alter wild-type cutting rates and therefore can be effectively lumped together with wild-type sites. (ii) HR repairs using mutated vs. wild-type templates are assumed to be equally efficient. Modifications could be made to the model to address these simplifications, but this is not considered here. It is also worth noting that, formally, given assumption ii above, the Markov process should actually stop should the condition $p_N^{(c)}=1$ be reached for some value of c, since at this point no wild-type sites remain to be cut, whereas what happens instead mathematically is that cuts continue but the model remains in a fixed state. Finally, the model effectively represents the mutation count distribution as a function of independent variable c (number of cuts) and not as a function of time. No prediction is made regarding the time rates of DNA repair or PERV site elimination, although time can be assumed to increase monotonically with c.

To analyze PERV elimination through the Markov model, N was always set to 62. However, since the relative efficiencies of perfect vs. mutagenic NHEJ repair are unknown (as noted above), and because relative rates of mutagenic NHEJ vs. HR repair can vary widely depending on cell state and type, the mutation count distributions for a discrete grid covering the complete two-dimensional space of all possible parameter values for n, m, and h, (2500 parameter combinations in all) was computed. The model was implemented both as a MatLab (Mathworks, Waltham) script and as an R script using the library markovchain (available as Supplemental Files modelMarkov.m, modelMarkov.R, respectively).

Figure 29A:
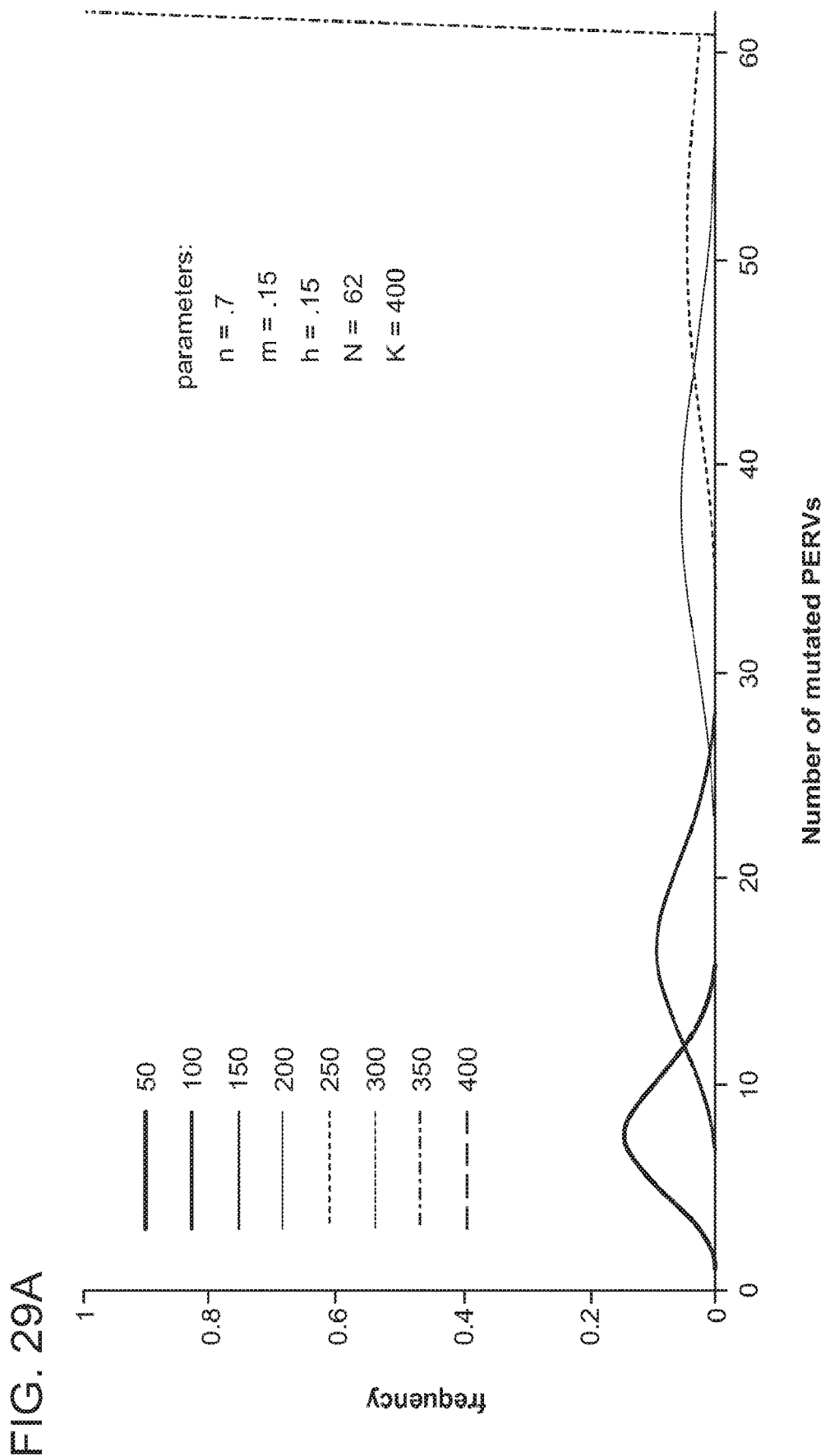
Figure 29C:
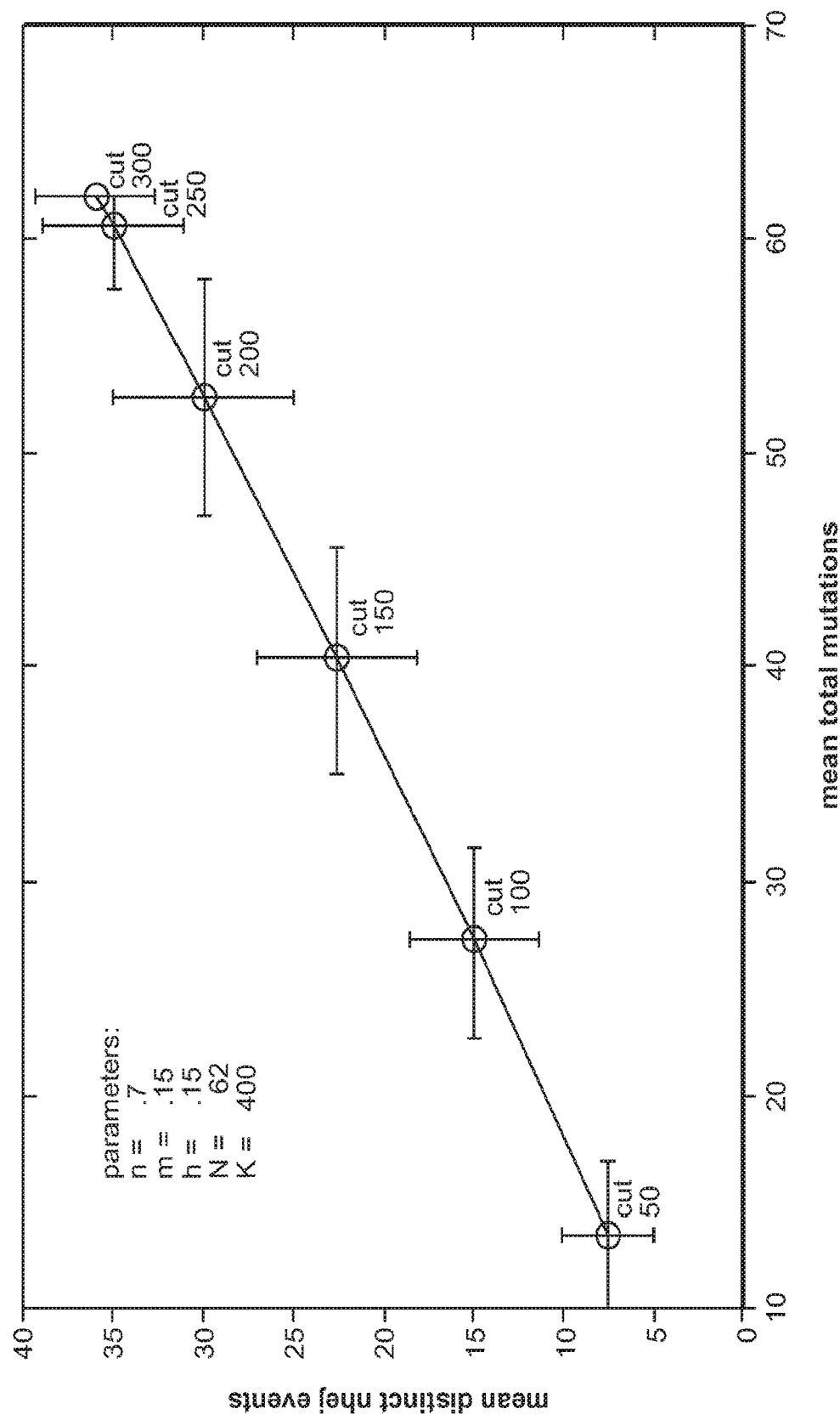
Figure 29D:
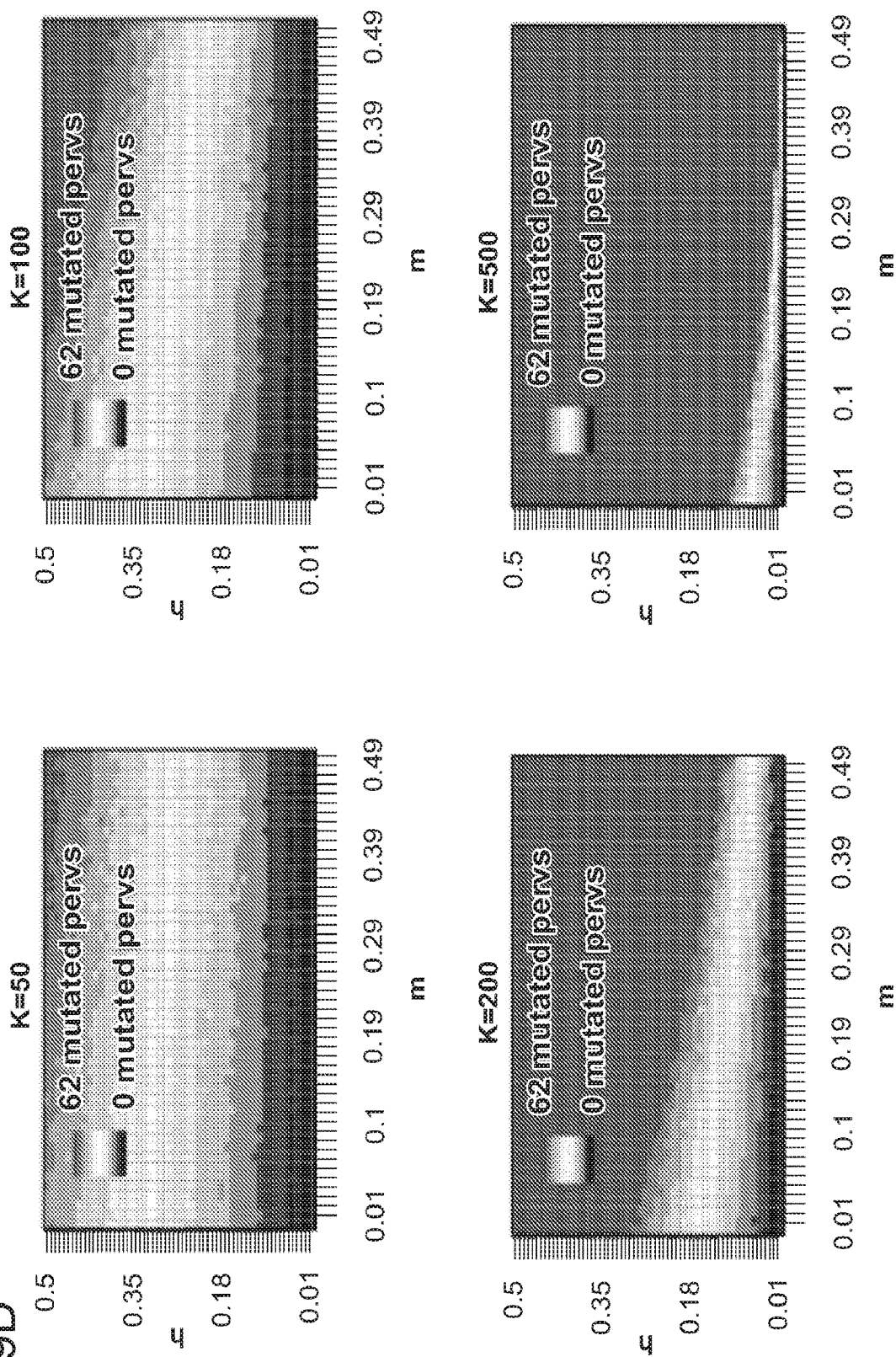

In addition to computing the mutation count distribution via the Markov model for particular parameter values, the MatLab script performed random simulations of the NHEJ and HR repair processes throughout a series of K cuts, allowing bivariate distributions of the numbers of total mutations vs. distinct NHEJ events to be estimated, illustrated in FIGS. 29B-29C. The R script was used to estimate the most likely state of the system over the grid of n, m, and h combinations described above. K was varied depending on the computation. As illustrated in FIG. 30, the invariable result of the model was a unimodal distribution of mutation counts whose mean advanced towards fixation at N mutations with c, and in FIGS. 29B-29C, K was set to a value high enough to demonstrate fixation. For the calculation of the most likely state of the system over the n, m, and h grid, K was set to 50, 100, 200, or 500, and 100 simulations were conducted for each parameter combination.

Data Deposition

Illumina Miseq data with PERVs elements genotyping data has been uploaded to the European Nucleotide Archive (ENA) hosted by the European Bioinformatics Institute (EBI) with the submission reference PRJEB11222.

Appendix A provide further information regarding various aspects of the present teachings, which is herein incorporated by reference in its entirety.

The DNA sequence listing further includes genome sequences of multiple endogenous retroviral elements extracted from pig genome sequence and from public sequence databases. (SEQ ID NO:30-280)

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10959413B2). An electronic copy of the "Sequence Listing" will also be available from the USPTO upon request and payment of the fee set forth in 37 CFR 1.19(b)(3).

What is claimed is:

1. A method of inactivating expression of at least 20% of the copies of an endogenous retroviral target gene in a cell comprising multiple copies of the gene, comprising:
   (a) introducing into the cell (i) one or more guide ribonucleic acid (gRNA) sequences that comprise a portion that is complementary to a portion of the endogenous retroviral target gene, and (ii) a nucleic acid sequence that encodes a Cas protein; and
   (b) maintaining the cells under conditions in which (i) the Cas protein is expressed, (ii) the Cas protein and gRNAs form co-localization complexes with a plurality of the copies of the endogenous retroviral target gene, and (iii) the Cas protein cuts at least 20% of the copies of the endogenous retroviral target gene, thereby inactivating expression of said copies.

2. The method of claim 1, wherein the cell is a stem cell, zygote, or a germ line cell.

3. The method of claim 1, wherein the cell is a porcine cell.

4. The method of claim 1, wherein the endogenous retroviral target gene is a porcine endogenous retrovirus (PERV) gene.

5. The method of claim 4, wherein the PERV gene comprises a pol gene.

6. The method of claim 5, wherein all copies of the pol gene in the cell are inactivated.

7. The method of claim 1, wherein the Cas protein is a Cas9.

8. The method of claim 1, wherein the one or more gRNA sequences are about 10 to about 1000 nucleotides.

* * * * *